(12) United States Patent
Bernardon et al.

(10) Patent No.: US 6,818,666 B2
(45) Date of Patent: Nov. 16, 2004

(54) BI-AROMATIC COMPOUNDS LINKED VIA A HETEROETHYLENE RADICAL, AND PHARMACEUTICAL AND COSMETIC COMPOSITIONS USING THEM

(75) Inventors: Jean-Michel Bernardon, Nice (FR); Philippe Diaz, Nice (FR)

(73) Assignee: Galderma Research & Development, Valbonne (FR)

( * ) Notice: Subject to any disclaimer, the term of this patent is extended or adjusted under 35 U.S.C. 154(b) by 103 days.

(21) Appl. No.: 10/215,202

(22) Filed: Aug. 9, 2002

(65) Prior Publication Data

US 2003/0100583 A1 May 29, 2003

Related U.S. Application Data

(60) Continuation-in-part of application No. 09/768,496, filed on Jan. 25, 2001, now Pat. No. 6,441,010, which is a division of application No. 09/269,977, filed as application No. PCT/FR98/01835 on Aug. 21, 1998, now Pat. No. 6,201,019.

(30) Foreign Application Priority Data

Aug. 21, 1919 (FR) .............................. 97 10554

(51) Int. Cl.$^7$ ...................... A61K 31/382; C07D 335/06
(52) U.S. Cl. ........................... 514/432; 549/23; 549/49; 549/398; 549/407; 549/408; 549/462; 514/443; 514/456; 514/469
(58) Field of Search ................................ 514/432, 443, 514/456, 469; 549/23, 49, 398, 407, 408, 462

(56) References Cited

U.S. PATENT DOCUMENTS

| 3,772,023 A | 11/1973 | Nakajima |
| 6,201,019 B1 | 3/2001 | Bernardon |
| 6,441,010 B2 | 8/2002 | Bernardon |

FOREIGN PATENT DOCUMENTS

| DE | 21 30 483 | 2/1972 |
| EP | 0 661 258 | 7/1995 |

OTHER PUBLICATIONS

Miura, Takashi et al; Addition of Phenyl Areneselenosulphonates to Acetylenes: A Route to Acetylenic Sulphones; J. Chem. Soc., Chem. Commun., 1982; Department of Chemistry, Tokyo Metropolitan University, Setagaya, Tokyo 158, Japan; Dec. 21, 1981; pp 438–439.

Latypova, V.Z. et al; 92:41060n Electrichemical Reactions of Sulfur–, Selenium–, and Tellurium–Containing Organic Compounds; (Kazan Gos. University, Kazan, USSR) Abstract—Zh. Obshch. Khim.; 1978; 48(12), 2681–5.

Kataeva, L.M., et al; 97:181555f UV Spectra of a Series of Acetylene Thioethers; Deposited Doc. 1981, SPSTL 193 khp–D81, 12 pp (USSR) Abstract.

Kargin, Yu, et al; Item 92:12818k Electrochemical Reaction of Sulfur–, Selenium–, and Tellurum–Containing Organic Compounds. III. Mechanism of the Electrochemical Reduction of some Ethynyl Thioethers in Dimethylformamide; (USSR) Abstract—Zh. Obshch. Khim. 1979, 49(10), 2267–71.

Latypova, et al. Electrichemical Reactions of S–, Se– and Te—Containing Organic Compounds, Zhurnal Obshchei Khimii, vol. 54, No. 4, pp. 848–851, Apr. 1984 (Russian and English text).

Beltrame et al, "Kinetics and mechanism of nucleophilic substitution of arylhaloacetylenes by sodium p–toluenethiolate in N, N–dimethylformamide", No. 1, 1973, pp. 63–66, Database Chemabs, Chemical Abstracts Service, Columbus, Ohio, US.

Latypova et al, "Electrochemical reactions to sulfur–, selenium–, and tellurium–containing organic compounds", vol. 54, No. 4, 1984, pp. 848–851, Database Chemabs, Chemical Abstracts Service, Columbus, Ohio, US.

Yu et al, "Structural Modifications of 6–Naphthalene–2–Carboxylate Retinoids", Bioorg. Med. Chem. Lett., vol. 6, No. 23, 1996, pp. 2865–2870.

Suzuki et al, A New Straightforward Synthesis of Alkynyl Sulfones via the Sonochemical Coupling Between Alkynyl Halides and Copper Sulfinates, Tetrahedron Lett., vol. 37, No. 21, 1996, pp. 3717–3720.

Diaz, P. et al: New Selenium–containing Acetylenic retinoids by direct coupling of alkynylsilanes with selenylhalides. Tetrahed. Lett. vol. 39, pp. 9003–9006 (1998).

*Primary Examiner*—Charanjit S. Aulakh
(74) *Attorney, Agent, or Firm*—Nixon & Vanderhye P.C

(57) ABSTRACT

Bi-aromatic compounds linked via a heteroethynylene radical are provided along with pharmaceutical and cosmetic compositions containing these compounds and methods for their use.

20 Claims, No Drawings

BI-AROMATIC COMPOUNDS LINKED VIA A HETEROETHYLENE RADICAL, AND PHARMACEUTICAL AND COSMETIC COMPOSITIONS USING THEM

The present application is a continuation-in-part of application Ser. No. 09/768,496 filed Jan. 25, 2001 (now U.S. Pat. No. 6,441,010, issued Aug. 27, 2002), which is a divisional of application Ser. No. 09/269,977, filed Apr. 8, 1999 (now U.S. Pat. No. 6,201,019, issued Mar. 13, 2001), which is a 371 U.S. national phase of PCT/FR98/01835, filed Aug. 21, 1998, and claims benefit of FR 97 10554, filed Aug. 21, 1997.

The invention relates, as novel and useful industrial products, to bi-aromatic compounds whose aromatic rings are linked via a divalent heteroethynylene radical. The invention also relates to the use of these novel compounds in pharmaceutical compositions intended for use in human or veterinary medicine, or alternatively in cosmetic compositions.

The compounds according to the invention have pronounced activity in the fields of cell differentiation and proliferation and find applications more particularly in the topical and systemic treatment of dermatological complaints associated with a keratinization disorder, dermatological (or other) complaints with an inflammatory and/or immunoalergic component, and dermal or epidermal proliferations, whether they are benign or malignant. These compounds can also be used in the treatment of connective tissue degenerative diseases, for combating ageing of the skin, whether this is light-induced or chronological ageing, and for treating cicatrization disorders. They moreover find an application in the opthalmological field, in particular in the treatment of corneopathy.

The compounds according to the invention can also be used in cosmetic compositions for body and hair hygiene.

Bi-aromatic compounds whose aromatic rings are linked via a divalent propynylene have already been described in EP-661,258 as active substances in pharmaceutical or cosmetic compositions.

The compounds according to EP-661,258 correspond to the following general formula:

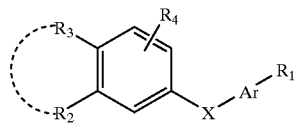

in which:

Ar is a divalent aromatic radical optionally substituted with a radical $R_5$ or a heteroaromatic radical optionally substituted with a radical $R_6$ when the hetero atom is nitrogen, $R_1$ represents H, —$CH_3$, —$CH_2OR_6$, —$OR_6$, —$COR_7$ or —$S(O)_tR_9$, t being 0, 1 or 2.

$R_2$ and $R_3$ represent H, $C_1$–$C_{20}$ alkyl, —$OR_6$ or —$SR_6$, or $R_2$ and $R_3$ taken together, form a 5- or 6-membered ring optionally substituted with methyl groups and/or optionally interrupted by an oxygen or sulphur atom, $R_4$ and $R_5$ represent H, a halogen, lower alkyl or —$OR_6$, $R_6$ represents H, lower alkyl or —$COR_9$, $R_7$ represents H, lower alkyl,

or —$OR_8$, $R_8$ represents H, linear or branched $C_1$–$C_{20}$ alkyl, alkenyl, mono- or polyhydroxyalkyl, optionally substituted aryl or aralkyl, or a sugar or amino acid or peptide residue, $R_9$ represents lower alkyl, R and R' represent H, lower alkyl, mono- or polyhydroxyalkyl, optionally substituted aryl or a sugar, amino acid or peptide residue or R and R', taken together, form a heterocycle, and X represents a divalent radical which, from right to left or vice-versa, has the formula:

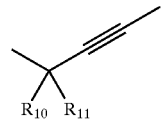

in which:

$R_{10}$ represents H, lower alkyl or —$OR_6$, $R_{11}$ represents —$OR_6$, or $R_{10}$ and $R_{11}$, taken together, form an oxo (=O) radical, and the salts of the said compounds of the above formula when $R_1$ represents a carboxylic acid function, and the optical and geometrical isomers of these said compounds.

The compounds according to the present invention differ from those of EP-661,258 essentially in that the radical X or divalent propynylene radical has been replaced with a divalent heteroethynylene radical.

The reason for this is that it has been found, surprisingly and unexpectedly, that this structural change makes it possible to significantly increase the pharmaceutical and cosmetic properties thereof and also to decrease certain side effects thereof.

A subject of the present invention is thus novel compounds which can be represented by the following general formula:

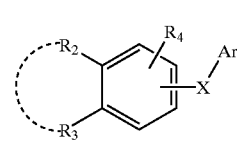

(I)

in which:

Ar represents a radical chosen from the formulae (a) to (c) below:

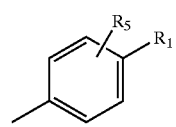

(a)

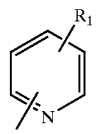

(b)

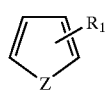

(c)

Z being O or S, or N—R$_6$,

R$_1$ represents a halogen atom, —CH$_3$, —CH$_2$—OR$_7$, —OR$_7$, —COR$_8$ or a polyether radical, R$_2$ and R$_3$, which may be identical or different, represent H, linear or branched C$_1$–C$_{20}$ alkyl, C$_3$–C$_{12}$ cycloalkyl, —OR$_7$ or —SR$_7$, at least one from among R$_2$ and R$_3$ being linear or branched C$_1$–C$_{20}$ alkyl or C$_3$–C$_{10}$ cycloalkyl, or R$_2$ and R$_3$, taken together, form a 5- or 6-membered ring, optionally substituted with at least one methyl and/or optionally interrupted by a hetero atom chosen from O and S, p R$_4$ and R$_5$ represent H, a halogen atom, linear or branched C$_1$–C$_{20}$ alkyl, —OR$_7$ or a polyether radical, R$_6$ represents H, linear or branched C$_1$–C$_{10}$ alkyl or —OCOR$_9$, R$_7$ represents H, linear or branched C$_1$–C$_{10}$ alkyl or —COR$_9$, R$_8$ represents H, linear or branched C$_1$–C$_{10}$, alkyl, —OR$_{10}$ or

R$_9$ represents linear or branched C$_1$–C$_{10}$ alkyl,

R$_{10}$ represents H, linear or branched C$_1$–C$_{20}$ alkyl, mono- or polyhydroxvalkyl, allyl, optionally substituted aryl or aralkyl, or a sugar residue, r' and r", which may be identical or different, represent H, C$_1$–C$_{10}$ alkyl, mono- or polyhydroxyalkyl, optionally substituted aryl, an amino acid or peptide residue, or, taken together with the nitrogen atom, form a heterocycle, X represents a divalent radical which, from right to left or vice-versa, has the formula:

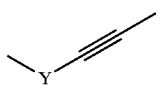

in which:

Y represents O, S(O)$_n$ or Se(O)$_{n'}$, n and n' being 0, 1 or 2, with the proviso that when n=2 and Ar is a radical of formula (a) above, in which R$_1$=—CH$_3$ and R$_5$=H, then at least one of the radicals R$_2$ or R$_3$ is other than —CH$_3$, and the salts of the compounds of formula (I) when R$_1$ represents a carboxylic acid function, as well as the optical isomers of the said compounds of formula (I).

When the compounds according to the invention are in the form of a salt, this is preferably a salt of an alkali metal or alkaline-earth metal, or alternatively of zinc or of an organic amine.

According to the present invention, the term "C$_1$–C$_{10}$ alkyl" preferably refers to the methyl, ethyl, isopropyl, butyl, tert-butyl, hexyl, 2-ethylhexyl and octyl radicals.

The term "linear or branched C$_1$–C$_{20}$ alkyl" refers in particular to the methyl, ethyl, propyl, 2-ethylhexyl, octyl, dodecyl, hexadecyl and octadecyl radicals.

The term "C$_3$–C$_{12}$ cycloalkyl radical" refers to a mono- or polycyclic radical, in particular the cyclopropyl, cyclopentyl, cyclohexyl, 1-methylcyclo-hexyl and 1-adamantyl radicals.

The term "polyether radical" refers to a radical containing from 2 to 5 carbon atoms interrupted by at least two oxygen atoms, such as the methyloxymethoxy, methoxyethoxy and methoxyethoxymethoxy radicals.

The term "monohydroxyalkyl" refers to a radical preferably containing 2 or 3 carbon atoms, in particular a 2-hydroxyethyl, 2-hydroxypropyl or 3-hydroxypropyl radical.

The term "polyhydroxyalkyl" refers to a radical preferably containing 3 to 6 carbon atoms and from 2 to 5 hydroxyl groups, such as the 2,3-dihydroxypropyl, 2,3,4-trihydroxybutyl and 2,3,4,5-tetrahydroxypentyl radicals or the pentaerythritol residue.

The term "aryl" preferably refers to a phenyl radical optionally substituted with at least one halogen atom, a hydroxyl or a nitro function.

The term "aralkylo" preferably refers to a benzyl or phenethyl radical optionally substituted with at least one halogen atom, a hydroxyl or a nitro function.

The term "sugar residue" refers to a residue derived in particular from glucose, from galactose or from mannose, or alternatively from glucuronic acid.

The term "amino acid residues" refers in particular to a residue derived from lysine, from glycine or from aspartic acid, and the term "peptide residue" refers more particularly to a dipeptide or tripeptide residue resulting from the combination of amino acids.

The term "heterocycle" preferably refers to a piperidino, morpholino, pyrrolidino or piperazino radical, optionally substituted in position 4 with a C$_1$–C$_6$ lower alkyl or a mono- or polyhydroxyalkyl as defined above.

When R$_1$, R$_4$ and/or R$_5$ represents a halogen atom, this is preferably a fluorine, chlorine or bromine atom.

According to a first preferred embodiment, the compounds according to the invention correspond to the following general formula:

(II)

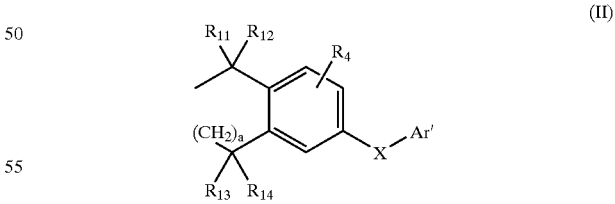

in which:

Ar' represents a radical of formula:

(a)

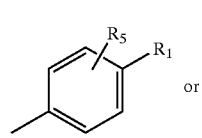

or

-continued

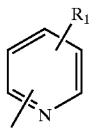
(b)

R₁, R₄, R₅ and X being as defined above for formula (I),
R₁₁, R₁₂, R₁₃ and R₁₄, which may be identical or different, represent H or —CH₃, and
n is 1 or 2.

According to a second preferred embodiment, the compounds according to the invention correspond to the following formula:

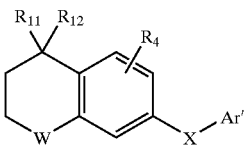
(III)

in which:
W represents O or S,
R₄, R₁₁, R₁₂, Ar' and X being as defined above in the formulae (I) and (II).

Lastly, according to a third preferred embodiment, the compounds according to the invention correspond to the following formula:

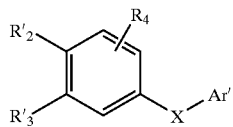
(IV)

in which:
R₄, Ar' and X are as defined above in formulae (I) to (III), and
at least one of the radicals R'₂ and/or R'₃ represents a mono- or polycyclic C₅–C₁₀ cycloalkyl radical, the other representing one of the meanings given for R₂ or R₃.

Among the compounds of formulae (I) to (IV) above, according to the present invention, mention may be made in particular of the following:

Methyl 4-(5,5,8,8-tetramethyl-5,6,7,8-tetrahydro-2-naphthylsulphanylethynyl)benzoate,
4-(5,5,8,8,-Tetramethyl-5,6,7,8-tetrahydro-2-naphthylsulphanylehynyl)benzoic acid,
Methyl 4-(5,5,8,8,-tetramethyl-5,6,7,8-tetrahydro-2-naphthylsulphonylethynyl)benzoate,
Methyl 4-(5,5,8,8,-tetramethyl-5,6,7,8-tetrahydro-2-naphthyloxyethynyl)benzoate,
4-(5,5,8,8,-Tetramethyl-5,6,7,8-tetrahydro-2-naphthyloxyethynyl)benzoic acid,
Methyl 4-(5,5,8,8,-tetramethyl-5,6,7,8-tetrahydro-2-naphthylsulphanylethynyl)benzoate,
4-(5,5,8,8,-Tetramethyl-5,6,7,8-tetrahydro-2-naphthylsulphanylethynyl)benzoic acid,
Methyl 4-(5,5,8,8,-tetramethyl-5,6,7,8-tetrahydro-2-naphthylsulphonylethynyl)benzoate,
4-(5,5,8,8,-Tetramethyl-5,6,7,8-tetrahydro-2-naphthylsulphonylethynyl)benzoic acid,
Methyl 4-(5,5,8,8,-tetramethyl-5,6,7,8-tetrahydro-2-naphthylsulphinylethynyl)benzoate,
4-(5,5,8,8,-Tetramethyl-5,6,7,8-tetrahydro-2-naphthylsulphinylethynyl)benzoic acid,
Methyl 4-(5,5,8,8,-tetramethyl-5,6,7,8-tetrahydro-2-naphthylselanylethynyl)benzoate,
4-(5,5,8,8,-Tetramethyl-5,6,7,8-tetrahydro-2-naphthylselanylethynyl)benzoic acid,
Methyl 2-hydroxy-4-(5,5,8,8,-tetramethyl-5,6,7,8-tetrahydro-2-naphthylselanylethynyl)benzoate,
2-Hydroxy-4-(5,5,8,8,-tetramethyl-5,6,7,8-tetrahydro-2-naphthylselanylethynyl)benzoic acid,
6-(4-methoxymethoxyphenylethynylselanyl)-1,1,4,4-tetramethyl-1,2,3,4-tetrahydronaphthalene,
Ethyl 6-(5,5,8,8,-tetramethyl-5,6,7,8-tetrahydro-2-naphthylselanylethynyl)nicotinate,
6-(5,5,8,8,-Tetramethyl-5,6,7,8-tetrahydro-2-naphthylselanylethynyl)nicotinic acid,
N-(4-Hydroxyphenyl)-4-(5,5,8,8,-tetramethyl-5,6,7,8-tetrahydro-2-naphthylselanylethynyl)benzamide,
Methyl 5-(5,5,8,8,-tetramethyl-5,6,7,8-tetrahydro-2-naphthylselanylethynyl)-2-pyridime carboxylate,
2-(4—Chlorophenylselanylethynyl)-5,5,8,8-tetramethyl-5,6,7,8-tetrahydronaphthalene,
Methyl 4-(3,5,5,8,8-pentamethyl-5,6,7,8-tetrahydro-2-naphthylselanylethynyl)benzoate,
4-(3,5,5,8,8-Pentamethyl-5,6,7,8-tetrahydro-2-naphthylselanylethynyl)benzaic acid,
Methyl 2-hydroxy-4-(3,5,5,8,8-pentamethlyl-5,6,7,8-tetahydro-2-naphthylselanylethynyl)benzoate,
2-Hydroxy-4-(3,5,5,8,8-pentamethyl-5,6,7,8-tetrahydro-2-naphthylselanylethynyl)benzoic acid,
Ethyl 6-(3,5,5,8,8-pentamethyl-5,6,7,8-tetrahydro-2-naphthylselanylethynyl)nicotinate,
6-(3,5,5,8,8-Pentamethyl-5,6,7,8-tetrahydro-2-naphthylselanylethynyl)nicotinic acid,
N-(4-Hydroxyphenyl)-6-(3,5,5,8,8-pentamethyl-5,6,7,8-tetrahydro-2-naphthylselanylethynyl)nicotinamide,
N-Butyl-6-(3,5,5,8,8-pentamethyl-5,6,7,8-tetrahydro-2-naphthylselanylethynyl)nicotinamide,
Morpholin-4-yl-[6-(3,5,5,8,8,-pentamethyl-5,6,7,8-tetrahydro-2-naphthylselanylethynyl)-3-pyridyl]methanone,
Methyl 5-(3,5,5,8,8-pentamethyl-5,6,7,8-tetrahydro-2-napathylselanylethynyl)pyridine-2-carboxylate,
5-(3,5,5,8,8-Pentamethyl-5,6,7,8-tetrahydro-2naphthylselanylethynyl)pyridine-2-carboxylic acid,
[4-(5,5,8,8-Tetramethyl-5,6,7,8-tetrahydro-2-naphthylselanylethynyl)phenyl]methanol,
Methyl 4-(5,5,8,8-tetramethyl-5,6,7,8-tetrahydro-2-naphthylethynylsulphanyl)benzoate,
Methyl 4-(5,5,8,8-tetramethyl-5,6,7,8-tetrahydro-2-naphthylethynylsulphonyl)benzoate,
Methyl 4-(5,5,8,8-tetramethyl-5,6,7,8-tetrahydro-2-naphthylethynylsulphinyl)benzoate,
4-(5,5,8,8-Tetramethyl-5,6,7,8-tetrahydro-2-naphthylethynylsulphanyl)benzoic acid,
4-(5,5,8,8-Tetramethyl-5,6,7,8-tetrahydro-2-naphthylethynylsulphonyl)benzoic acid,
4-(5,5,8,8-Tetramethyl-5,6,7,8-tetrahydro-2-naphthylethynylsulphinyl)benzoic acid,
4-(3,5,5,8,8-Pentamethyl-5,6,7,8-tetrahydro-2-naphthylselanylethynyl)phenol, Ethyl 4-(4-hydroxy-5,5,8,8-tetramethyl-5,6,7,8-tetrahydro-2-naphthylselanylethynyl)benzoate, Ethyl 4-(4-methoxymethoxy-5,5,8,8-tetramethyl-5,6,7,8-tetrahydro-2-naphthylselanylethynyl)benzoate, 4-(4-Methoxymethoxy-5,5,8,8-tetramethyl-5,6,7,8-tetrahydro-2-naphthylselanylethynyl)benzoic acid, 4-(4-Pentyloxy-5,5,8,8-tetramethyl-5,6,7,8-tetrahydro-2-naphthylselanylethynyl)benzoic acid, Ethyl 4-(3-methoxymethoxy-5,5,8,8-tetramethyl-5,6,7,8-tetrahydro-2-naphthylselanylethynyl)benzoate, Ethyl 4-(3-methoxyethoxymethoxy-5,5,8,8-tetramethyl-5,6,7,8-tetrahydro-2-naphthylselanylethynyl)benzoate, 4-(3-Methoxyethoxymethoxy-5,5,8,8-tetramethyl-5,6,7,8-tetrahydro-2-naphthylselanylethynyl)benzoic acid, 4-(3-Methoxymethoxy-5,5,8,8-tetramethyl-5,6,7,8-tetrahydro-2-naphthylselanylethynyl)benzoic acid, Ethyl 4-(3-pentyloxy-5,5,8,8-tetramethyl-5,6,7,8-tetrahydro-2-naphthylselanylethynyl)benzoate, 4-(3-Pentyloxy-5,5,8,8-tetramethyl-5,6,7,8-tetrahydro-2-naphthylselanylethynyl)benzoic acid,

[4-(5,5,8,8-Tetramethyl-5,6,7,8-tetrahydro-2-naphthylselanylethynyl)phenyl]carbaldehyde, Methyl 4-(4,4-dimethylthiochroman-8-ylselanylethynyl)benzoate, 4-(4,4-Dimethylthiochroman-8-ylselanylethynyl)benzoic acid, Methyl 4-(5,5,8,8-tetramethyl-5,6,7,8-tetrahydro-8-naphthylselanylethynyl)benzoate, 4-(5,5,8,8-Tetramethyl-5,6,7,8-tetrahydro-8-naphthylselanylethynyl)benzoic acid, Methyl 4-[3-(1-adamantyl)-4-methoxyphenyl)-1-ylselanylethynyl]benzoate, 4-[3-(1-Adamantyl)-4-methoxyphenyl))-1-ylselanylethynyl]benzoic acid, Methyl 4-[4-(1-adamantyl)-3-methoxyphenyl)-1-ylselanylethynyl]benzoate, and 4-[4-(1-Adamantyl)-3-methoxyphenyl)-1-ylselanylethynyl]benzoic acid.

A subject of the present invention is also the processes for preparing the compounds of formula (I) above according to the reaction schemes given in Tables A and B.

With reference to Table A, the compounds of formula (I) in which X represents the divalent radical

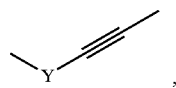

i.e. the compounds of formula (Ia), can be obtained according to two different synthetic routes depending on whether Y=oxygen or Y≠oxygen.

When X=oxygen, the starting material is the compound of formula (1), which, in the presence of a base such as potassium hydride or sodium hydride, is then coupled with trichloroethylene. The dichloroethylene product obtained, of formula (2), is then subjected to the action of a lithiated base, such as butyllithium, in a solvent such as THF, to give the acetylenic compound of formula (3). This acetylene is then coupled with an aryl halide or a heteroaryl halide, preferably an iodo derivative, in the presence of a palladium catalyst to give the compounds of formula (IIa) with Y=oxygen.

When Y≠oxygen, the lithium acetylide of formula (5) is first prepared, from the aromatic or heteroaromatic acetylenic compound (4), in the presence of a lithiated derivative such as butyllithium, in a solvent such as THF. Starting with the lithium acetylide (5), which is not isolated, a coupling is carried out with the compound of formula (6), in a solvent such as THF, to give the compounds of formula (Ia) with Y≠oxygen.

Starting with these compounds of formula (Ia) in which Y=S or Se, it is possible to gain access to the oxidized derivatives by oxidation using an oxidizing agent such as meta-chloroperbenzoic acid (mCPBA) or sodium periodate.

With reference now to Table B, the compounds of formula (I), in which X represents a divalent radical

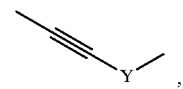

i.e. the compounds of formula (Ic), can also be obtained according to two different synthetic routes depending an whether Y=oxygen or Y≠oxygen.

When Y=oxygen, the starting material is an aromatic or heteroaromatic compound of formula (7), which, in the presence of a base such as potassium hydride or sodium hydride, in a solvent such as THF, is then coupled with trichloroethylene. The dichloro-ethylene product obtained (8) is then subjected to the action of a lithiated base such as butyllithium, in THF, to give the oxoacetylenic compound of formula (9). This acetylene is then coupled with an aryl halide (10), preferably an iodo derivative, in the presence of a palladium catalyst, to give the compounds of formula (Ic) with Y=oxygen.

When Y≠oxygen; the starting material is an aromatic acetylenic compound of formula (11), which is converted into a lithiated derivative in the presence of butyllithium, for example in a solvent such as THF. The lithiated acetylenic derivative (12), which is not isolated, is then coupled with an aromatic or heteroaromatic compound of formula (13), the coupling reaction being carried out in a solvent such as THF. The compounds of formula (Ic) with Y≠oxygen are thus obtained by this synthetic route.

Starting with these compounds of formula (Ic), in which Y=S or Se, it is also possible to obtain the oxidized derivatives by oxidation using an oxidizing agent such as meta-chloroperbenzoic acid (mCPBA) or sodium periodate.

When, in the compounds according to the invention, the radical $R_1$ represents —COOH, these radicals are prepared by protecting the carboxylic acid function with a protecting group or the alkyl type.

By saponification of ester function in the presence of a base such as sodium hydroxide or lithium hydroxide in an alcoholic solvent or in THF, the corresponding free acids are thus obtained.

When $R_1$ is —OH, the compounds can be obtained from the corresponding acid by reduction in the presence of hydride such as boron hydride.

When $R_1$ is —CH=O, the compounds can be obtained by oxidation of the corresponding alcohols using manganese oxide or pyridinium dichromate.

When $R_1$ is

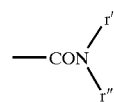

the compounds can be obtained by conversion of the corresponding acid into the acid chloride, for example with thionyl chloride, followed by reaction with aqueous ammonia or a suitable amine.

A subject of the present invention is also the compounds of formula (I) as defined above, as medicinal products.

The compounds of general formula (I) have agonist or antagonist activity with respect to the expression of one or more biological markers in the test of differentiation of mouse embryonic teratocarcinoma cells (F9) (Skin Pharmacol. 3, p. 256–267, 1990) and/or on the in vitro differentiation of human keratinocytes (Skin Pharmacol. 3, p. 70–85, 1990). These abovementioned tests show the activities of the compounds in the fields of differentiation and proliferation. The activities can also be measured in cellular transactivation tests using RAR recombinant receptors according to the method by B. A. Bernard et al., Biochemical and Biophysical Research Communication, vol. 186, 977–983, 1992.

The compounds according to the invention are particularly suitable in the following fields of treatment:

1) for treating dermatological complaints associated with a keratinization disorder which has a bearing on differentiation and on proliferation, in particular for treating common acne, comedones, polymorphonuclear leukocytes, rosacea, nodulocystic acne, acne conglobata, senile acne and secondary acne such as solar, medication-related or occupational acne,
2) for treating other types of keratinization disorder, in particular ichthyosis, ichthyosiform states, Darier's disease, palmoplantar keratoderma, leucoplasias and leucoplasiform states, and cutaneous or mucous (buccal) lichen,
3) for treating other dermatological complaints associated with a keratinization disorder with an inflammatory and/or immunoallergic component and, in particular, all forms of psoriasis, whether it is cutaneous, mucous or ungual psoriasis and even psoriatic rheumatism, or alternatively cutaneous atopy, such as eczema or respiratory atopy or alternatively gingival hypertrophy; the compounds can also be used in certain inflammatory complaints which have no keratinization disorder;
4) for treating all dermal or epidermal proliferations, whether benign or malignant and whether they are of viral origin or otherwise, such as common warts, flat warts and verruciform epidermodysplasia, it being also possible for the oral or florid papillomatoses and the proliferations to be induced by ultraviolet radiation, in particular in the case of basocellular and spinocellular epithelioma,
5) for treating other dermatological disorders such as bullosis and collagen diseases,
6) for treating certain ophthalmological disorders, in particular corneopathies,
7) for repairing or combating ageing of the skin, whether this is light-induced or chronological ageing, or for reducing actinic keratoses and pigmentations, or any pathologies associated with chronological or actinic ageing,
8) for preventing or curing the stigmata of epidermal and/or dermal atrophy induced by local or systemic corticosteroids, or any other form of cutaneous atrophy,
9) for preventing or treating cicatrization disorders or for preventing or repairing stretch marks,
10) for combating disorders of sebaceous functioning such as the hyperseborrhoea of acne or simple seborrhoea,
11) in the treatment or prevention of cancerous or precancerous states,
12) in the treatment of inflammatory complaints such as arthritis,
13) in the treatment of any general or skin complaint of viral origin,
14) in the prevention or treatment or alopecia,
15) in the treatment of dermatological or general complaints having an immunological component, and 16) in the treatment of complaints of the cardiovascular system such as arteriosclerosis.

In the therapeutic fields mentioned above, the compounds according to the invention mar be employed advantageously in combination with other compounds of retinoid-type activity, with D vitamins or derivatives thereof, with corticosteroids, with anti-free-radical agents, α-hydroxy or α-keto acids or derivatives thereof, or alternatively with ion-channel blockers. The expression "D vitamins or derivatives thereof" means, for example, vitamin $D_2$ or $D_3$ derivatives and in particular 1,25-dihydroxyvitamin $D_3$. The expression "anti-free-radical agents" means, for example, α-tocopherol, superoxide dismutase or SOD, ubiquinol or certain metal-chelating agents. The expression "α-hydroxy or α-keto acids or derivatives thereof" means, for example, lactic, malic, citric, glycolic, mandelic, tartaric, glyceric or ascorbic acid or the salts, amides or esters thereof. Lastly, the term "ion-channel blockers" means, for example, Minoxidil (2,4-diamino-6-piperidinopyrimidine-3-oxide) and derivatives thereon.

A subject of the present invention is also pharmaceutical compositions containing at least one compound of formula (I) as defined above, one of the optical or geometrical isomers thereof or one of the salts thereof.

The pharmaceutical compositions are intended in particular for treating the abovementioned complaints, and are characterized in that they comprise a pharmaceutically acceptable support which is compatible with the mode of administration selected, at least one compound of formula (I), one of the optical or geometrical isomers thereof or one of the salts thereof.

The compounds according to the invention may be administered enterally, parenterally, topically or ocularly.

Via the enteral route, the compositions may be in the form of tablets, gelatin capsules, sugar-coated tablets, syrups, suspensions, solutions, powders, granules, emulsions, microspheres or nanospheres or polymeric or lipid vesicles which enable controlled release. Via the parenteral route, the compositions may be in the form of solutions or suspensions for infusion or for injection.

The compounds according to the invention are generally administered at a daily dose of about 0.01 mg/kg to 100 mg/kg of body weight taken in 1 to 3 doses.

Via the topical route, the pharmaceutical compositions based on compounds according to the invention are more particularly intended for the treatment of the skin and the mucosae and may then be in the form of ointments, creams, milks, salves, powders, impregnated pads, solutions, gels, sprays, lotions or suspensions. They may also be in the form of microspheres or nanospheres or polymeric or lipid vesicles or polymeric patches and hydrogels which enable controlled release of the active principle. Furthermore, these topical-route compositions may either be in anhydrous form or in aqueous form, depending on the clinical indication.

Via the ocular route, they are mainly eyedrops.

These compositions for topical or ocular use contain at least one compound of formula (I) as defined above, or one of the optical or geometrical isomers thereof or alternatively one of the salts thereof, at a concentration preferably of between 0.001% and 5% by weight relative to the total weight of the composition.

The compounds of formula (I) according to the invention also find an application in the cosmetic field, in particular in body and hair hygiene and especially for treating skin types with a tendency towards acne, for promoting the regrowth of the hair, for combating hair loss, for combating the greasy appearance of the skin or the hair, in protection against the harmful effects of the sun or in the treatment of physiologically dry skin types, and for preventing and/or combating light-induced or chronological ageing.

In the cosmetic field, the compounds according to the invention can moreover be employed advantageously in combination with other compounds of retinoid-type activity, with D vitamins or derivatives thereof, with corticosteroids, with anti-free-radical agents, α-hydroxy or α-keto acids or derivatives thereof, or alternatively with ion-channel blockers, all or these latter compounds being as defined above.

The present invention is thus also directed towards a cosmetic composition which is characterized in that it comprises, in a cosmetically acceptable support, at least one compound of formula (I) as defined above or one of the optical or geometrical isomers thereof or one of the salts thereof, it being possible for the said cosmetic composition to be, in particular, in the form or a cream, a milk, a lotion, a gel, microspheres or nanospheres or polymeric or lipid vesicles, a soap or a shampoo.

The concentration of compound of formula (I) in the cosmetic compositions according to the invention is advantageously between 0.001% and 3% by weight relative to the total weight of the composition.

The pharmaceutical and cosmetic compositions according to the invention can also contain inert additives or even pharmacodynamically or cosmetically active additives or combinations of these additives and, in particular: wetting agents; depigmenting agents such as hydroquinone, azelaic acid, caffeic acid or kojic acid; emollients; moisturizing agents such as glycerol, PEG-400, thiomorpholino and derivatives thereof, or urea; anti-seborrhoea or anti-acne agents such as S-carboxymethylcysteine, S-benzylcysteamine, the salts or derivatives thereof, or benzoyl peroxide; antibiotics such as erythromycin and esters thereof, neomycin, clindamycin and esters thereof, and tetracyclines; antifungal agents such as ketoconazole or 4,5-polymethylene-3-isothiazolidones; agents for promoting the regrowth of the hair, such as Minoxidil (2,4-diamino-6-piperidinocyrimidine-3-oxide) and derivatives thereof, Diazoxide (7-chloro-3-methyl-1,2,4-benzothiadiazine 1,1-dioxide) and Phenytoin (5,4-diphenyl-imidazolidine-2,4-dione); non-steroidal anti-inflammatory agents; carotenoids and, in particular, β-carotene; anti-psoriatic agents such as anthraline and derivatives thereof and, lastly, eicosa-5,8,11, 14-tetraynoic acid and eicosa-5,8,11-triynoic acid, the esters and amides thereof.

The compositions according to the invention may also contain flavour-enhancing agents, preserving agents such as para-hydroxybenzoic acid esters, stabilizing agents, moisture regulators, pH regulators, osmotic pressure modifiers, emulsifying agents, UV-A and UV-B screening agents, and antioxidants such as α-tocopherol, butylated hydroxyanisole or butylated hydroxytoluene.

Several examples for obtaining the active compounds of formula (I) according to the invention, as well as various cosmetic and pharmaceutical formulations based on such compounds, will now be given for illustrative purposes and with no limiting nature.

EXAMPLES

Example 1

Methyl 4-(5,5,8,8,-tetramethyl-5,6,7,8-tetrahydro-2-nachthylsuphanylethynyl)-benzoate (a) Methyl 4-trimethylsilylethynylbenzoate 21.5 g (0.1 mol) of methyl 4-bromobenzoate, 300 ml of triethylamine and a mixture of 200 mg of palladium acetate and 400 mg of triphenylphosphine are introduced into a three-necked flask. 20 g (0.204 mol) of trimethylsilylacetylene are then added, after which the mixture is heated gradually to 90° C. over 1 hour and left at this temperature for 5 hours. The reaction medium is then cooled, the salt is filtered of and the filtrate is evaporated. The residue is taken up in 200 ml of hydrochloric acid (5%) and 400 ml of ethyl ether. The ether phase is separated out after settling has taken place, washed with water, dried over magnesium sulphate and evaporated. The residue obtained is purified by chromatography on a column of silica eluted with dichloromethane. After evaporation of the solvents, 23 g (100%) of the expected derivative are collected in the form of a colourless oil.

(b) Methyl 4-ethynylbenzoate 38.33 g (226 mmol) of the product obtained above in 300 ml of methanol are introduced into a three-necked flask. 125 g of potassium carbonate are then added and the medium is stirred for 48 hours at room temperature. The solvent is evaporated off and the residue obtained is purified by chromatography on a column of silica eluted with dichloromethane. After evaporation of the solvents, the residue is taken up in heptane and, after filtration, 32 g (100%) of the expected derivative are collected in the form of a straw-yellow solid.

(c) Methyl 4-(5,5,8,8,-tetramethyl -5,6,7,8-tetrahydro-2-naphthylsulphanylethynyl)benzoate A 2.5 M solution of butyllithium in hexane (20 mmol, 8.1 ml) is added to a solution of methyl 4-ethynylbenzoate (3 g, 18.7 mmol) in THF (300 ml) at −78° C. The temperature is maintained for 45 minutes and is then raised to −40° C. A solution of 5,6,7,8-tetrahydro-5,5,3,8-tetramethyl-2-naphthalene disulphide (J. Med. Chem. 1995, 38, 3171) (16.5 g, 37.4 mmol) in THF (60 ml) is then added at this temperature. The reaction medium is then stirred for 1 hour at 0° C., after which it is poured into a mixture of ethyl ether and saturated ammonium chloride solution. The organic phase is washed twice with water, dried over anhydrous magnesium sulphate and concentrated on a rotary evaporator under vacuum at 40° C. After chromatography on a column of silica, using a mixture of heptane/methylene chloride (60/40), and after evaporation, 1.9 g of a white solid (27%) are obtained.

$^1$H (CDCl$_3$): 1.28 (6H, s), 1.30 (6H, s), 1.69 (4H, s), 3.92 (3H, s), 7.25 to 7.31 (2H Ar, m), 7.42 (1H Ar, d, J=2 Hz), 7.50 (1H, Ar, d, J=7.5 Hz), 8.00 (1H, Ar, d, J=7.5 Hz).

13$_c$ (CDCl$_3$): 32.25 (CH$_3$), 34.60 (C), 35.02 (C), 35.36 (CH$_2$), 52.68 (OCH$_3$), 81.26 (C), 96.96 (C), 124.82 (CH Ar), 125.56 (CH Ar), 128.29 (C Ar), 128.37 (CH Ar), 128.85 (C Ar), 129.88 (C Ar), 130.04 (2 CH Ar), 131.29 (2 CH Ar), 144.66 (C, Ar), 146.88 (C Ar), 166.95 (COO).

Example 2

4-(5,5,8,8-Tetramethyl-5,6,7,8-tetrahydro-2-naphthylsuphanylethynyl)benzoic acid A solution of methyl 4-(5,5,8,8-tetramethyl-5,6,7,8-tetrahydro-2-naphthylsulphanylethynyl)benzoate (590 mg, 1.6 mmol) and of lithium hydroxide (383 mg, 9.3 mmol) in THF is refluxed for 24 hours. The reaction mixture is poured into an Et$_2$O/water mixture, acidified to pH 1 with concentrated hydrochloric acid solution, and extracted once with ethyl ether. After separation of the phases by settling, the organic phase is washed twice with water, dried over magnesium sulphate and concentrated on a rotary evaporator under vacuum at 40° C. The solid obtained is crystallized from heptane and 440 mg (77%) of a white solid are obtained. m.p. (melting point)=193.50° C.

NMR δ ppm: $^1$H (CDCl$_3$): 1.28 (6H, s), 1.30 (6H, s), 1.69 (4H, s), 7.29 to 7.32 (2H Ar, m), 7.42 (1H Ar, d, J=2 Hz), 7.53 (1H Ar, d, J=8, 5 Hz), 8.08 (1H Ar, d, J=8.5 Hz).

13$_c$ (CDCl$_3$): 31.44 (CH$_3$), 33.80 (C), 34.22 (C), 34.54 (CH$_2$), 81.30 (C), 100.01 (C), 124.06 (CH Ar), 124.81 (CH Ar), 127.59 (CH Ar), 127.94 (C Ar), 128.46 (C Ar), 129.87 (2 CH Ar), 130.49 (2 CH Ar), 143.93 (C Ar), 146.12 (C Ar), 171.06 (COO).

Example 3

Methyl 4-(5,5,8,8-tetramethyl-5,6,7,8-tetrahydro-2-naphthylsuphonylethynyl)benzoate A solution of meta-perbenzoic acid (700 mg) in CHCl$_3$ (12 ml) is added dropwise, at 0° C., to a solution of the product of Example 1 (500 mg, 1.3 mmol) in 6 ml of CHCl$_3$. After stirring for 1 hour, the mixture is concentrated on a rotary evaporator under vacuum. After chromatography on a column of silica with a heptane/methylene chloride mixture (30/70), 280 mg of a white solid are obtained (52%).

$^1$H (CDCl$_3$): 1.32 (6H, s), 1.34 (6H, s), 1.73 (4H, s), 3.93 (3H, s), 7.51 (2H Ar, d, J=8.3 Hz), 7.60 (2H Ar, d, J=8.5 Hz), 7.78 (1H Ar, dd, J1=8.5 Hz, J2=2 Hz), 7.98 to 8.05 (3H Ar, m).

13$_c$ (CDCl$_3$) : 31.63 (CH$_3$), 31.73 (CH$_3$), 34.58 (CH$_2$), 34.64 (CH$_2$), 34.85 (C), 34.98 (C), 52.52 (CH$_3$), 87.77 (C), 90.99 (C), 122.61 (C Ar), 124.35 (CH Ar), 125.99 (CH Ar), 128.04 (CH Ar), 129.68 (CH Ar), 132.44 (C Ar), 132.69 (CH Ar), 138.37 (C Ar), 152.50 (C Ar), 165.83 (COO).

Example 4

Methyl 4-(5,5,8,8-tetramethyl-5,6,7,8-tetrahydro-2-naphthylselanylethynyl)benzoate
(a) 5,6,7,8-Tetrahydro-5,5,8,8-tetramethyl-2-naphthalene diselenide A 1.7 M solution of tert-butyllithium in pentane (37.4 mmol, 22 ml) is added to a solution of 2-bromo-5,6,7,8-tetrahydro-5,5,8,8-teramethyl-naphthalene (4.22 g, 15.8 mmol) in THF (100 ml) at −78° C. over 10 min. The mixture is stirred at 0° C. for 30 min. Selenium (1.33 g, 16.8 mmol) is added in two portions. The mixture is stirred at 0° C. for 15 min and then at room temperature for 30 min. 1N HCl solution (40 ml) is added and the reaction mixture is then treated with ethyl ether. The organic phase is washed twice with water, dried over anhydrous magnesium sulphate and concentrated on a rotary evaporator under vacuum at 40° C. 10 ml of ethanol and 50 mg of sodium hydroxide are added to the oil obtained. The mixture is stirred vigorously for a few minutes and is then concentrated on a rotary evaporator under vacuum at 40° C. The solid obtained is filtered through silica (eluted with heptane) and then crystallized from an ethanol/ether mixture. After filtration, 2.9 g (69%) of an orange-coloured solid are obtained.

$^1$H NMR (CDCl$_3$): 1.21 (6H, s), 1.25 (6H, s), 1.65 (4H, s), 7.20 (1H Ar, d, J=8.25 Hz), 7.38 (1H Ar, dd, J=1.9 Hz, J=8.25 Hz), 7.51 (1H Ar, d, J=1.9 Hz).

(b) Methyl 4-(5,5,8,8-tetramethyl-5,6,7,8-tetrahydro-2-naphthylselanylethynyl)benzoate Bromine (0.15 ml, 2.9 mmol) is added to a solution of 5,6,7,8-tetrahydro-5,5,8,8-tetramethyl-2-naphthalene diselenide (1.5 g, 2.8 mmol) in THF (3 ml). The mixture is stirred at room temperature for 2 h and the solvent is then removed. Copper iodide (2.15 g, 11.3 mmol), methyl 4-ethynylbenzoate (810 mg, 5 mmol) obtained according to Example 1(b) and DMF (15 ml) are added. The reaction mixture is stirred at room temperature for 3 h and is then treated with ethyl ether and aqueous ammonia solution. The organic phase is washed twice with water, dried over anhydrous magnesium sulphate and concentrated on a rotary evaporator under vacuum at 40° C. The residue is recrystallized from heptane and, after filtration, 1.8 g (75%) of a white powder are obtained. m.p.=90-1° C.

$^1$H NMR (CDCl$_3$): 1.28 (6H, s), 1.30 (6H, s), 1.69 (4H, s), 3.92 (3H, s), 7.29 (1H Ar, d, J=8.3 Hz), 7.36 (1H Ar, dd, J=1.9 Hz, J=8.3 Hz), 7.48 to 7.53 (3H Ar, m), 7.98 (2H Ar, d, J=8.5 Hz).

Example 5

4-(5,5,8,8-Tetramethyl-5,6,7,8-tetrahydro-2-naphthylselanylethynyl)benzoic acid

Lithium hydroxide (440 mg) is added to a solution of methyl 4-(5,5,8,8-tetramethyl-5,6,7,8-tetrahydro-2-naphthylselanylethynyl)benzoate (740 mg, 1.74 mmol), obtained in Example 4, in 15 ml of THF and 2 ml of a water/methanol mixture (1/1). The reaction medium is refluxed for 8 h. It is then poured into an ethyl ether/water mixture, acidified to pH 1 with concentrated hydrochloric acid solution and extracted with ethyl ether. After separation of the phases by settling, the organic phase is washed twice with water, dried over anhydrous magnesium sulphate and concentrated on a rotary evaporator under vacuum at 40° C. The residue is recrystallized from heptane. After filtration, 615 mg (86%) of a white powder are obtained. m.p.=182° C.

$^1$H NMR (CDCl$_3$): 1.28 (6H, s), 1.30 (6H, s) , 1.69 (4H, s), 7.29 (1H Ar, d, J=8.3 Hz), 7.36 (1H Ar, dd, J=1.9 Hz, J=8.3 Hz), 7.52 to 7.55 (3H Ar, m), 8.07 (2H Ar, d, J=8.5 Hz).

Example 6

Methyl 2-hydroxy-4-(5,5,8,8-tetramethyl-5,6,7,8-tetrahydro-2-naphthylselanylethynyl)benzoate
(a) Methyl 4-trimethylsilanylethynyl-2-hydroxybenzoate In a manner similar to that of Example 1(a), starting with 4.00 g (14.4 mmol) of methyl 4-iodo-2-hydroxybenzoate, 3.07 g (86%) of the expected compound are obtained in the form of an orange-coloured oil.

$^1$H NMR (CDCl$_3$): 0.06 (s, 9H), 3.75 (s, 3H), 6.76 (dd, 1H, J=8.2/1.5 Hz), 6.87 (d, 1H, J=1.4 Hz), 7.56 (d, 1H, J=8.2 Hz), 10.53 (s, 1H).

(b) Methyl 4-ethynyl-2-hydroxybenzoate 3.07 g (12.4 mmol) of methyl 4-trimethylsilanylethynyl-2-hydroxybenzoate are mixed, in a 500 ml three-necked flask, with 50 ml of THF, and 13.7 ml of a tetrabutylammonium fluoride solution (1 M/THF) are added dropwise. The reaction medium is stirred for 1 h at room temperature and is then poured into water and extracted with ethyl ether. After separation of the phases by settling, the organic phase is dried over magnesium sulphate and concentrated. 2.48 g (100%) of a beige-coloured powder are obtained. m.p.=62° C.

$^1$H NMR (CDCl$_3$): 3.21 (s, 1H), 3.96 (s, 3H), 6.98 (dd, 1H, J=8.2/1.5 Hz), 7.10 (d, 1H, J=1.3 Hz), 7.78 (d, 1H, J=8.2 Hz), 10.76 (s, 1H).

(c) Methyl 2-hydroxy-4-(5,5,8,8-tetramethyl-5,6,7,8-tetrahydro-2-naphthylselanylethynyl)benzoate In a manner similar to that of Example 4(b), after reaction of 1.5 g (2.8 mmol) of 5,6,7,8-tetrahydro-5,5,8,8-tetramethyl-2-naphthalene diselenide, in 2 ml of THF, with bromine (0.15 ml, 2.9 mmol), copper iodide (2.15 g; 11.3 mmol) and methyl 4-ethynyl-2-hydroxybenzoate (890 mg; 5 mmol) in 10 ml of DMF are added. After purification on a column of silica (dichloromethane 10/heptane 90), 2.15 g (97%) of the expected ester derivative are obtained in the form of a yellow solid. m.p.=70° C.

$^1$H NMR (CDCl$_3$): 1.28(d, 12H); 1.69(s, 4H); 3.95(s, 3H); 6.94(dd, 1H); 7.04(d, 1H); 7.26 to 7.37(m, 2H); 7.51(d, 1H); 7.77(d, 1H); 10.77(s, 1H).

$^{-}$C NMR (CDCl$_3$): 31.8; 4*CH3/34.2; Cq/34.6; Cq/34.9; 2*CH2/52.4; CH3/75.1; Cq/101.6; Cq/111.9; Cq/119.7; CH/121.9; CH/124.5; Cq/127.0; CH/127.8; CH/128.1; CH/129.9; CH/130.4; Cq/144.7; C/146.7; Cq/161.2; Cq/170.1; Cq.

Example 7

2-Hydroxy-4-(5,5,8,8-tetramethyl)-5,6,7,8-tetrahydro-2-nauhthylselanylethynyl)benzoic acid A solution of 2-hydroxy-4-(5,5,8,8-tetramethyl-5,6,7,8-tetrahydro-2-naphthylselanylethynyl)benzoate (1.2 g; 2.72 mmol) obtained in Example 6(c) and sodium hydroxide (1.5 g; 37.5 mmol) in 20 ml of THF is refluxed for 24 h. The reaction medium is then poured into an ethyl acetate/water mixture, acidified to pH 1 with concentrated hydrochloric acid solution and extracted once with ethyl acetate. After separation of the phases by settling, the organic phase is washed twice with water, dried over magnesium sulphate and concentrated on a rotary evaporator under vacuum at 40° C. 1 g (86%) of a yellow solid is obtained. m.p.=170° C.

$^1$HNR (DMSO): 1.28(m, 12H); 1.68(s, 4H); 6.95(d, 1H); 7.03(s, 1H); 7.25 to 7.37(m, 2H); 7.51(s, 1H); 7.83(d, 1H).

$^{-}$C NMR (DMSO): 31.8; 4*CH3/34.2; Cq/34.6; Cq/34.9; 2*CH2/76.0; Cq/101.5; Cq/119.7; CH/122.1; CH/124.4; Cq/127.1; Cq/127.9; CH/128.2; CH/130.9; CH/131.4; Cq/144.7; Cq/146.7; Cq/161.6; Cq/174.2; Cq.

Example 8

6-(4-Methoxymethoyphenylethynylselanyl)-1,1,4,4-tetramethyl-1,2,3,4-tetrahydronaphthalene (a) 1-Iodo-4-methoxymethoxybenzene 5 g (22.7 mmol) of 4-iodophenol are added to a suspension or 75% sodium hydride (872 mg; 27.25 mmol) in 20 ml of dimethylformamide. The mixture is stirred for 30 minutes at room temperature and 2.59 ml (34.1 mmol) of methoxymethyl chloride are then added. The solution is stirred for 2 h and the medium is then poured into an ethylacetate/water mixture. After separation of the phases by settling, the organic phase is washed twice with water, dried over magnesium sulphate and concentrated on a rotary evaporator under vacuum at 40° C. 5.74 g (96%) of a colourless oil are obtained.

$^1$H NMR (CDCl$_3$): 3.45(s, 3H); 5.13(s, 2H); 6.80(d, 2H); 7.55(d, 2H)

$^{-}$C NMR (CDCl$_3$): 56.0; CH3/84.3; Cq/94.3; CH2/118.4; 2*CH/138.2; 2*CH/157.0; Cq (b) 1-Trimethylsilylethynyl-4-methoxymethoxybenzene 5.74 g (21.7 mmol) of 1-iodo-4-methoxymethoxybenzene, 100 ml or triethylamine and a mixture of 1.53 g (2.18 mmol) of dichloro-bis (triphenylphosphine)palladium and 831 mg (4.37 mmol) of copper iodide are introduced into a three-necked flask. 6.14 ml (43.5 mmol) of trimethylsilylacetylene are then added and the medium is stirred for 48 h at room temperature. It is then poured into a water/ethyl acetate mixture. The organic phase is washed twice with water and, after separation of the phases by settling, it is washed with magnesium sulphate and concentrated.

(c) 1-Ethynyl-4-methoxymethoxybenzene

In a manner similar to that of Example 1(b), by reaction of the product obtained according to Example 8(b) with 50 ml of methanol and with potassium carbonate for 15 h at room temperatures and after purification on a column of silica (dichloromethane 20/heptane 80), 840 mg (24%) of the expected product are obtained in the form of a yellow oil.

$^1$H NMR (CDCl$_3$)): 3.00(s, 1H); 3.46(s, 3H); 5.17(s, 2H); 6.97(d, 2H); 7.42(d, 2H).

$^{-}$C NMR (CDCl$_3$): 56.1; CH3/76.1; Cq/83.5; CH/94.2; CH2/115.4; Cq/116.1; CH/133.6; CH/157.6; Cq (d) 6-(4-Methoxymethoxyphenylethynylselanyl-1,1,4,4-tetramethyl-1,2,3,4-tetrahydronaphthalene In a manner similar to that of Example 4(b), after reaction of 1.3 g (2.44 mmol) of 5,6,7,8-tetrahydro-5,5,8,8-tetramethyl-2-naphthalene diselenide, in 2 ml of THF, with bromine (0.13 ml, 2.5 mmol), copper iodide (1.86 g; 9.8 mmol) and 1-ethynyl-4-methoxymethoxybenzene (713 mg; 4,4 mmol) in 10 ml of DMF are added. After purification on a column of silica (dichloromethane 20/heptane 80), 1.7 g (90%) of the expected derivative are obtained in the form of a yellow oil.

$^1$H NMR (CDCl$_3$): 127(m, 12H); 1.67(s, 4H); 3.47(s, 3H); 5.18(s, 2H); 6.98(dd, 2H); 7.01 to 7.51(m, 5H).

$^{-}$C NMR (CDCl$_3$): 31.8; 4*CH3/34.1; Cq/34.5; Cq 34.9; 2*CH2/56.1; CH3/68.3; Cq/77.5; Cq/102.0; Cq/116.1; 2*Ch/116.7; Cq/125.3; Cq/133.3; 2*CH/144.2; Cq/146.5; Cq/157.4; Cq.

Example 9

6-(5,5,8,8-Tetramethyl-5,6,7,8-tetrahydro-2-naphthylselanylethynyl)nicotinic acid (a) Ethyl 6-trimethylsilylethynyl-3-pyridine-carboxylate In a manner similar to that of Example 1(a), starting with 4 g (14.4 mmol) of methyl 6-iodo-3-pyridinecarboxylate, 3.29 g (92%) of the expected compound are obtained in the form of a beige-coloured powder. m.p.=55° C.

$^1$H NMR (CDCl$_3$) δ 0.10 (s, 9H), 1.22 (t, 2H, J=7.1 Hz), 4.23 (q, 3H, J=7.1 Hz), 7.33 (d, 1H, J=8.2 Hz), 8.06 (dd, 1H, J=8.1/2.1 Hz), 8.97 (d, 1H, J=2.1 Hz).

(b) Ethyl 6-ethynylnicotinate

In a manner similar to that of Example 6(b), starting with 3.29 g (13.3 mmol) of ethyl 6-trimethylsilylethynylnicotinate, 1.00 g (43%) of the expected compound is obtained in the form of beige-coloured flakes. m.p.=35° C.

$^1$H NMR (CDCl$_3$) δ 1.42 (t, 3H, J=7.1 Hz), 3.33 (s, 1H), 4.42 (q, 2H, J=7.2 Hz), 7.56 (d, 1H, J=8.1 Hz), 8.28 (dd, 1H, J=8.1/2.1 Hz), 9.18 (d, 1H, J=2.0 Hz)

(c) Ethyl 6-(5,5,8,8-tetramethyl-5,6,7,8-tetrahydro-2-naphthylselanylethynyl)nicotinate In a manner similar to that of Example 4(b), after reaction of 1.84 g (3.4 mmol) of 5,6,7,8-tetrahydro-5,5,8,8,-tetramethyl-2-naphthalene diselenide, in 2 ml of THF, with bromine (0.18 ml, 3.49 mmol), copper iodide (2.64 g; 13.9 mmol) and ethyl 6-ethynylnicotinate (1 g; 5.7 mmol) in 10 ml of DMF are added. 1.95 g (78%) of the expected derivative are obtained in the form of a brown oil.

$^1$H NMR (CDCl$_3$): 1.28 to 1.30(m, 12H); 1.40(t, 3H); 1.69(s, 4H); 4.41(q, 2H); 7.12 to 7.59(m, 4H); 8.24(dd, 1H); 9.16(d, 1H).

(d) 6-(5,5,8,8-Tetramethyl-5,6,7,8-tetrahydro-2-naphthylselanylethynyl)nicotinic acid In a manner similar to that of Example 7, by reaction of 600 mg (1.36 mmol) of ethyl 6-(5,5,8,8-tetramethyl-5,6,7,8-tetrahydro-2-naphthylselanylethynyl)nicotinate in 30 ml of THF and 1 g of sodium hydroxide, and after trituration from heptane, 200 mg (36%) of the expected compound are obtained in the form of a yellow solid. m.p.=128° C.

$^1$H NMR (CDCl$_3$): 1.27 to 1.30(m, 12H); 1.68(s, 4H); 7.26 to 7.52(m, 5H); 8.32(d, 1H); 9.26(s, 1H)

$^{13}$C NMR (CDCl$_3$): 31.8; 4*CH3/34.2; Cq/34.6; Cq/34.8; CH2/34.9; CH2/78.6; Cq/101.4; Cq/123.6; Cq/123.8; Cq/125.8; CH/127.8; CH/128.4; CH/128.5; 137.9; CH/145.1; Cq/146.8; Cq/147.0; Cq/151.5; CH/169.0; Cq.

Example 10

N-(4-hydroxyphenyl)-4-(5,5,8,8-tetramethyl-5,6,7,8-tetrahydro-2-naphthylselanylethynyl)benzamide A solution of 250 mg (0.63 mmol) of 4-(5,5,8,8-tetramethyl-5,6,7,8-tetrahydro-2-naphthylselanylethynyl)benzoic acid obtained in Example 5, 169 mg (1.25 mmol) of 1-hydroxybenzoctriazole, 240 mg (1.25 mmol) of 1-(3-dimethylaminopropyl)-3-ethylcarbodiimide (EDC) and 82 mg (0.75 mmol) of 4-aminophenol in 20 ml of THF is stirred at room temperature for 15 h. Water and ethyl acetate are then added. After stirring and separation of the phases by settling, the aqueous phase is extracted with ethyl acetate. The organic phases are then combined and washed with water, dried over magnesium sulphate and concentrated on a rotary evaporator under vacuum at 40° C. The product is purified on a column of silica (ethyl acetate 20/heptane 80). 200 mg (65%) of a white solid are obtained. m.p.=202° C.

$^1$H NMR (DMSO): 1.23 (s, 6H); 1.25 (s, 6H); 1.64 (s, 4H); 6.72 to 6.76 (d, 2H); 7.39 (c, 1H); 7.51 to 7.55 (d, 2H); 7.59 to 7.61 (d, 2H); 7.64 to 7.67 (d, 2H); 7.95 to 7.98 (d, 2H); 9.28 (s, 1H); 10.10 (s, 1H).

Example 11

Methyl 5-(5,5,8,8-tetramethyl-5,6,7,8-tetrahydro-2-naphthylselanylethynyl)-2-pyridinecarboxylate (a) Methyl 5-trimethylsilylethynyl-2-pyridinecarboxylate In a manner similar to that of Example 1(a) starting with 7 g (26.6 mmol) of methyl 5-iodo-2-pyridinecarboxylate, 4.25 g (63%) of the expected compound are obtained in the form of an orange-coloured powder. m.p.=45° C.

$^1$H NMR (CDCl$_3$) δ 0.28 (s, 9H), 4.01 (s, 3H), 7.87 (dd, 1H, J=8.1/2.0 Hz), 8.08 (d, 1H, J=8.1 Hz), 8.77 (d, 1H, J=1.3 Hz).

(b) Methyl 5-ethynyl-2-pyridinecarboxylate

In a manner similar to that of Example 6(b), starting with 2.25 g (9.6 mmol) of methyl 5-trimethylsilylethynyl-2-pyridinecarboxylate, 380 mg (24%) of the expected compound are obtained in the form of a yellow powder. m.p.=40–5° C.

$^1$H NMR (CDCl$_3$) δ 3.40 (s, 1H), 4.02 (s, 3H), 7.93 (dd, 1H, J=8.1/2.0 Hz), 8.12 (d, 1H, J=8.1 Hz), 8.83 (d, 1H, J=1.9 Hz).

(c) Methyl 5-(5,5,8,8-tetramethyl-5,6,7,8-tetrahydro-2-naphthylselanylethynyl)-2-pyridinecarboxylate In a manner similar to that of Example 4(b), after reaction of 918 mg (1.73 mmol) of 5,6,7,8-tetrahydro-5,5,8,8-tetramethyl-naphthalene-2-diselenide in 2 ml of THF, with bromine (0.092 ml, 1.78 mmol), copper iodide (1.62 g; 8.5 mmol) and methyl 5-ethynyl-2-pyridinecarboxylate (500 mg; 3.1 mmol) in 10 ml of DMF are added. After trituration from heptane, 420 mg (32%) of the expected derivative are obtained in the form of a yellow solid. m.p.=75° C.

$^1$H NMR (CDCl$_3$): 1.28 to 1.29(d, 12H); 1.69(s, 4H); 4.02(s, 3H); 7.27 to 7.37(m, 2H); 7.54(d, 1H); 7.84(dd, 1H); 8.11(d, 1H); 8.77(s, 1H).

$^{13}$C NMR (CDCl$_3$): 31.7; 4*CH3/34.2; Cq/34.6; Cq/34.8; 2*CH/53.0; CH3/79.2; Cq/98.3; Cq/123.9; 2Cq/124.5; CH/127.4; CH/128.2; CH/128.3; CH/138.7; CH/145.1; CH/145.8; Cq/146.9; Cq/151.6; CH/165.2; Cq.

Example 12

2-(4–Chlorophenylselanylethynyl)-5,5,8,8,tetramethyl-5,6,7,8-tetrahydronaphthalene In a manner similar to that of Example 4(b), after reaction of 2 g (5.25 mmol) of bis(4-chlorophenyl) diselenide in 5 ml of THF with bromine (0.266 ml, 5.15 mmol), copper iodide (4.11 g: 21.6 mmol) and 6-ethynyl-1,1,4,4-tetramethyl-1,2,3,4-tetrahydronaphthalene (2.18 g; 10 mmol) (described in patent application EP 0,661,258 A1) in 20 ml of DMF are added, and after purification on a column of silica (heptane), 1.85 g (45%) of the expected derivative are obtained in the form of a colourless oil.

$^1$H NMR (CDCl$_3$): 1.28(s, 12H); 1.68(s, 4H); 7.26 to 7.30(m, 4H); 7.46 to 7.52(m, 3H).

Example 13

Methyl 4-(3,5,5,8,8-pentamethyl-5,6,7,8-tetrahydro-2-naphthylselanylethynyl)benzoate (a) 5,6,7,8-Tetrahydro-3,5,5,8,8-pentamethyl-2-naphthalene diselenide In a manner similar to that of Example 4(a), by reaction of 4.4 g (15.8 mmol) of 2-bromo-(5,6,7,8-tetrahydro-3,5,5,8,8-pentamethylnaphthalene) with 22 ml of tert-butyllithium and selenium (1.33 g, 16.8 mmol) in 100 ml of THF, 3.26 g (74%) of the expected selenated derivative are obtained in the form of a yellow solid. (m.p.=126° C.).

$^1$H NMR (CDCl$_3$): 1.14(6H, s), 1.23 (6H, s), 1.61 (4H, s), 2.35 (3H, s), 7.05 (1H Ar, s), 7.55 (1H Ar, s).

(b) Methyl 4-(3,5,5,8,8-pentamethyl-5,6,7,8-tetrahydro2-naphthylselanylethynyl)benzoate In a manner similar to that of Example 4(b), after reaction of 1.5 g (2.75 mmol) of 5,6,7,8-tetrahydro-3,5,5,8,8-pentamethyl-2-naphthalene diselenide in 5 ml of THF, with bromine (0.15 ml, 2.9 mmol), copper iodide (2.1 g; 11.05 mmol), and methyl 4-ethynylbenzoate (790 mg; 4.94 mmol) in 20 ml of DMF are added, and after trituration from heptane, 1.57 g (70%) of the expected derivative are obtained in the form or a white solid. m.p.=104° C.

$^1$H NMR (CDCl$_3$): 1.27 to 1.29(m, 12H); 1.68(s, 4H); 2.36(s, 3H); 3.91(s, 3H); 7.12(s, 1H); 7.50(d, 2H); 7.73(s, 1H); 8.00(d, 2H).

$^{13}$C NMR (CDCl$_3$): 21.4; CH3/32.3; 2*CH3/32.4; 2*CH3/34.5; Cq/34.8; Cq/35.5; 2*CH2/52.7; CH3/75.0; Cq/102.2; Cq/125:9; Cq/128.5; Cq/129.1; 2*CH/129.8; Cq/130.1; 2*CH/131.5; 2*CH/134.9; Cq/144.7; Cq/145.3; Cq/167.0; Cq.

Example 14

4-(3,5,5,8,8-Pentamethyl-5,6,7,8-tetrahydro-2-napthylselanylethynyl)benzoic acid In a manner similar to that of Example 7, by reaction of 1.35 g (3.07 mmol) of methyl 4-(3,5,5,8,8-pentamethyl-5,6,7,8-tetrahydro-2-napthylselanylethynyl)benzoate in 20 ml of THF and 3 g of sodium hydroxide, and after trituration from heptane, 1.05 g (80%) of the expected compound are obtained in the form of a white solid. m.p.=240° C.

$^1$H NMR (CDCl$_3$): 1.27 to 1.30(m, 12H); 1.68(s, 4H); 2.35(s, 3H); 7.13(s, 1H); 7.50(d, 2H); 7.71(s, 1H); 8.00(d, 2H).

$^{13}$C NMR (CDCl$_3$): 20.5; CH3/31.5; 4*CH3/33.6; Cq/33.9; Cq/34.6; 2*CH2/73.6; Cq/101.6; Cq/125.0; Cq/127.1; Cq/127.9; CH/128.3; CH/129.4; 2*CH/130.5; 2*CH/133.8; Cq/143.9; 2*Cq/144.5; Cq/167.5; Cq.

Example 15

Methyl-2-hydroxy-4-(3,5,5,8,8-pentamethyl-5,6,7,8-tetrahydro-2-napthylselanylethynyl)benzoate In a manner similar to that of Example 4(b), after reaction of 1 g (1.78 mmol) of 5,6,7,8-tetrahydro-3,5,5,8,8-pentamethyl-2-naphthalene diselenide in 5 ml of THF with bromine (0.092 ml, 1.78 mmol), copper iodide (1.36 g; 7.15 mmol) and methyl 4-ethynyl-2-hydroxybenzoate (566 mg; 3.2 mmol) obtained according to Example 6(b) in 10 ml of DMF are added, and after trituration from heptane, 715 mg (49%) of the expected derivative are obtained in the form of a brown solid. m.p.=102° C.

$^1$H NMR (CDCl$_3$): 1.20(s, 6H); 1.23(s, 6H); 1.60(s, 4H); 2.28(s, 3H); 3.87(s, 3H); 6.87(dd, 1H); 6.97(d, 1H); 7.04(s, 1H); 7.64(s, 1H); 7.71(d, 1H); 10.70(s, 1H).

$^{13}$C NMR (CDCl$_3$): 20.7; CH3/31.7; 4*CH3/33.8; Cq/34.1; Cq/34.8; 2*CH2/74.9; Cq/101.4; Cq/111.7; Cq/119.4; Cq/121.6; CH/125.1; Cq/128.4; 2*CH/129.7; CH/130.3; Cq/134.2; Cq/144.1; Cq/144.7; Cq/161.1; Cq/169.9; Cq.

Example 16

2-Hydroxy-4-(3,5,5,8,8-pentamethyl-5,6,7,8-tetrahydro-2-naphthylselanylethynyl)benzoic acid In a manner similar to that of Example 7, by reaction of 500 mg (1.1 mmol) of methyl 2-hydroxy-4-(3,5,5,8,8-pentamethyl-5,6,7,8-tetrahydro-2-naphthylselanylethynyl) benzoate, in 20 ml of THF, with 500 mg of sodium hydroxide, 464 mg (99%) of the expected compound are obtained in the form of a brown solid. m.p.=248° C.

$^1$H NMR (CDCl$_3$+DMSO): 0.89(s, 6H); 0.92(s, 6H); 1.30(s, 4H); 1.96(s, 3H); 6.55(dd, 1H); 6.60(s, 1H); 7.31(s, 1H) 7.43(d, 1H); 10.96(sb, 1H).

$^{13}$C NMR (CDCl$_3$+DMSO): 20.6; CH3/31.6; 4*CH3/34.0; Cq/34.6; Cq/34.7; 2*CH2/74.1; Cq/101.6; Cq/112.5; Cq/118.9; CH/121.3; CH/125.0; Cq/128.0; CH/128.3; CH/129.6; Cq/130.4; CH/133.9; Cq/144.0; Cq/144.0; Cq/144.5; Cq/161.4; Cq/171.9; Cq.

Example 17

Ethyl 6-(3,5,5,9,8-pentamethyl-5,6,7,8-tetrahydro-2-naphthylselanylethynyl)nicotinate In a manner similar to that of Example 4(b), after reaction of 1 g (1.78 mmol) of 5,6,7,8-tetrahydro-3,5,5,8,8-pentamethyl-2-naphthalene diselenide, in 5 ml of THF, with bromine (0.092 ml, 1.78 mmol), copper iodide (1.36 g; 7.15 mmol) and ethyl 6-ethynylnicotinate (463 mg; 2.64 mmol) in 10 ml of DMF are added, and 1.06 g (88%) of the expected derivative are obtained in the form of a brown solid. m.p.=95° C.

$^1$H NMR (CDCl$_3$): 1.20(s, 6H); 1.24(s, 6H); 1.34(t, 3H); 1.61(s, 3H); 4.33(q, 2H); 7.07(s, 1H); 7.38(d, 1H); 7.67(s, 1H); 8.17(dd, 1H); 9.08(d, 1H).

$^{13}$C NMR (CDCl$_3$): 13.9; CH3/20.9; CH3/31.5; 4*CH3/33.7; Cq/34.0; Cq/34.6; 2*CH2/61.2; CH2/77.2; Cq/101.2; Cq/124.2; Cq/124.3; Cq/125.2; Cq/128.4; Cq/129.4; Cq/134.8; Cq/136.8; Cq/144.0; Cq/145.1; Cq/146.3; Cq/150.8; Cq/164.5; Cq.

Example 18

6-(3,5,5,8,8-Pentamethyl-5,6,7,8-tetrahydro-2-naphthylselanylethynyl)nicotinic acid In a manner similar to that of Example 7, by reaction of 800 mg (1.73 mmol) of ethyl 6-(3,5,5,8,8-pentamethyl-5,6,7,8-tetrahydro-2-naphthylselanylethynyl)nicotinate, in 20 ml of THF, with 800 mg of sodium hydroxide, and after purification or a column of silica (ethyl acetate), 135 mg (19%) of the expected compound are obtained in the form of a yellow solid. m.p.=185° C.

$^1$H NMR (CDCl$_3$): 1.27(s, 6H); 1.31(s, 6H); 1.68(s, 4H); 2.40(s, 3H); 7.15(s, 1H); 7.26(s, 1H); 7.49(d, 1H); 7.74(s, 1H); 8.32(d, 1H); 9.25(s, 1H).

$^{13}$C NMR (CDCl$_3$): 21.7; CH3/32.2; 4*CH3/34.5, Cq/34.7; Cq/35.3; 2*CH2/78.9; Cq/101.7; Cq/124.0; Cq/124.9; Cq/126.1; CH/129.1; CH/130.2; CH/135.6; Cq/1382; CH/144.8; Cq/145.9; Cq/147.6; Cq/152.0; CH/169.5; Cq.

Example 19

N-(4-Hydroxyphenyl)-6-(3,5,5,8,8-pentamethyl-5,6,7,8-tetrahydro-2-napthylselanylethynyl)nicotinamide In a manner similar to that of Example 10, by reaction of 300 mg (0.72 mmol) of the 6-(3,5,5,8,8-pentamethyl-5,6,7,8-tetrahydro-2-naphthylselanylethynyl)nicotinic acid with 194 mg (1.45 mmol) of 1-hydroxybenzotriazole, 300 mg (1.45 mmol) of 1,3-dicyclohexylcarbodiimide and 95 mg (0.87 mmol) of 4-aminophenol in 20 ml of THF, and after purification on a column of silica (ethyl acetate 20/heptane 80), 20 mg (6%) of a yellow solid are obtained. m.p.=172° C.

$^1$H NMR (DMSO): 1.17 to 1.19(m, 12H); 1.56(s, 4H); 2.27(s, 3H); 6.68(d, 2H); 7.21(s, 1H); 7.46(d, 2H); 7.58(d, 1H); 7.64(s, 1H); 8.22(dd, 1H); 8.99(s, 1H)9.30(s, 1H); 10.2(s, 1H).

$^{13}$C NMR (DMSO): 31.6; 4*CH3/33.5; CH2/33.8; CH2/34.0; Cq/34.5,Cq/47.6; CH3/74.9; Cq/102.0; Cq/115.2; 2*CH/122.3; 2*CH/124.4; Cq/125.9; CH/128.7; CH/128.9; CH/130.4; Cq/134.8; Cq/136.1; CH/144.0; Cq/144.1; Cq/145.1; Cq/149.3; Cq/154.1; Cq/156.8; Cq.

Example 20

N-Butyl-6-(3,5,5,8,8-pentamethyl-5,6,7,8-tetrahydro-2-naphthylselanylethynyl)nicotinamide In a manner similar to that of Example 10, 300 mg (0.72 mmol) of 6-(3,5,5,5,8,8-pentamethyl-5,6,7,8-tetrahydro-2-naphthylselanylethynyl)nicotinic acid are reacted with 194 mg (1.45 mmol) of 1-hydroxybenzotriazole, 300 mg (1.45 mmol) of 1,3-dicyclohexylcarbodiimide and 63.5 mg (0.87 mmol) of butylamine in 20 ml of THF. After purification on a column of silica (ethyl acetate 20/heptane 80), 60 mg (17%) of a yellow solid are obtained. m.p.=172° C.

$^1$H NMR (CDCl$_3$): 0.97(t, 3H); 1.27 to 1.37(m, 12H); 1.37 to 1.46(m, 4H); 1.68(s, 4H); 2.39(s, 3H); 3.47(q, 2H) 6.13(m, 1H) 7.14(s, 1H); 7.46(d, 1H); 7.74(s, 1H); 8.07(dd, 1H); 8.87(s, 1H).

¹³C NMR (CDCl₃) 31.8; CH3/20.2; CH2/21.2; CH3/31.7; 4*CH3/34.0; Cq/34.3; Cq/35.0; 2*CH2/40.0; CH2/76.2; Cq/101.2; Cq/124.7 Cq/126.0; CH/128.7; CH/129.7; CH/; CH/35.1; Cq/135.3; CH;/144.3; Cq/145.4; Cq/145.5; Cq/; Cq.

Example 21

Morpholin-4-yl-[6-(3,5,5,8,8-pentamethyl-5,6,7,8-tetrahydro-2-naphthylselanylethynyl)-3-pyridyl]methanone In a manner similar to that of Example 10, 300 mg (0.72 mmol) of 6-(3,5,5,8,8-pentamethyl-5,6,7,8-tetrahydro-2-naphthylselanylethynyl)nicotinic acid are reacted with 194 mg (1.45 mmol) of 1-hydroxybenzotriazole, 300 mg (1.45 mmol) of 1,3-dicyclohexylcarbodiimide and 75.7 mg (0.87 mmol) of morpholine in 20 ml of THF. After purification on a column of silica (ethyl acetate 20/heptane 80), 60 mg (17%) of a colourless oil are obtained.

¹H NMR (CDCl₃): 1.27 to 1.32(m, 12H); 1.68(s, 4H); 2.39(s, 3H); 3.81(sbr, 8H); 7.13(s, 1H); 7.45(d, 1H); 7.71 to 7.75(m, 2H); 8.61(d, 1H).

¹³C NMR (CDCl₃): 21.2; CH3/31.8; 4*CH3/34 1; Cq/34.3; Cq/35.0; 2CH2/66.8; 4*CH2/75.5; Cq/101.1; Cq/124.7; Cq/126.0; CH/128.7; CH/129.4; Cq/129.7; CH/135.1; Cq/135.5; CH/144.3; Cq/144 5; Cq/145.4; Cq/148.3; CH/167.4; Cq.

Example 22

Methyl 5-(3,5,5,8,8-pentamethyl-5,6,7,8-tetrahydro-2-naphthylselanylethynyl)-2-pyridinecarboxylate In a manner similar to that of Example 4(b), after reaction of 945 mg (1.68 mmol) of 5,6,7,8-tetrahydro-3,5,5,8,8-pentamethyl-2-naphthalene diselenide, in 5 ml THF, with bromine (0.092 ml, 1.78 mmol), copper iodide (1.32 g; 6.95 mmol) and methyl 5-ethynyl-2-pyridinecarboxylate (500 mg; 3.1 mmol) in 10 ml of DMF are added, and after trituration from heptane, 1 g (73%) of the expected derivative is obtained in the form of a yellow solid. m.p.=52° C.

¹H NMR (CDCl₃) 1.27 to 1.29(m, 12H); 1.68(s, 4H); 2.37(s, 3H); 4.02(s, 3H) 7.14(s, 1H); 7.71(s, 1H); 7.85(dd, 1H) 8.02(s, 1H) 8.11(d, 1H).

¹³C NMR (CDCl₃): 20.7; CH3/31.5; 2*CH3/31.6; 2*CH3/33.7; Cq/34.0; Cq/34.6; 2*CH2/52.7; CH3/78; Cq/98.1; Cq/123.7; Cq/124.2;CH/124.5; Cq/128.4; CH/128.5; CH/134.3;Cq/138.3; CH/144.0; Cq/144.9; Cq/145.5;Cq/151.2; CH/162.2; Cq.

Example 23

5-(3,5,5,8,8-Pentamethyl-5,6,7,8-tetrahydro-2-naphthylselanylethynyl)-2-pyridinecazboxylic acid In a manner similar to that of Example 7, by reaction of 800 mg (1.73 mmol) of methyl 5-(3,5,5,8,8-pentamethyl-5,6,7,8-tetrahydro-2-naphthylselanylethynyl)-2-pyridinecarboxylate, in 20 ml of THF, with 2 g of sodium hydroxide, and after trituration from heptane, 580 mg (65%) of the expected compound are obtained in the form of a white solid. m.p.=164° C.

¹H NMR (CDCl₃): 1.28(s, 6H); 1.30(s, 6H); 1.69(s, 4H); 2.39(s, 3H); 7.16(s, 1H); 7.69(s, 1H); 7.93(d, 1H); 8.17(dbr, 1H); 8.66(sbr, 1H).

¹³C NMR (CDCl₃): 21.2; CH3/31.8; 2*CH3/3.9; 2*CH3/34.1; Cq/34.3; Cq/34.9; 2*CH2/124.6; Cq/128.8; CH/129.3; CH/134.9; Cq/139.8; CH/144.4; 2*Cq/145.5; 2*Cq.

Example 24

[4-(5,5,8,8-Tetramethyl-5,6,7,8-tetrahydro-2-naphthylselanylethyl)-phenyl]methanol A 1M solution of diisobutylaluminium hydride in toluene (4 ml, 4 mmol) is added dropwise, at 0° C., to a solution of methyl 4-(5,5,8,8-tetramethyl-5,6,7,8-tetrahydro-2-naphthylselanylethynyl)-benzoate obtained according to Example 4 (750 mg, 1.8 mmol), in toluene (20 ml) The solution is stirred for 4 h at 0° C. and is then treated with a double potassium sodium tartrate solution, filtered and taken up in a mixture of ethyl ether and water. The organic phase is washed with water, dried over magnesium sulphate and concentrated on a rotary evaporator under vacuum at 40° C. 418 mg (60%) of a colourless oil are obtained.

¹H NMR (CDCl₃): 1.26(s, 6H), 1.28(s, 6H), 1.76(s, 4H), 4.67(s, 2H), 7.24 to 7.37(m, 4H), 7.46(d, 2H, J=8.2 Hz), 7.52(d, 1H, J=1.9 Hz).

Example 25

Methyl 4-(5,5,8,8-tetramethyl-5,6,7,8-tetrahydro-2-naphthylethynylsulphanyl)-benzoate In a manner similar to that of Example 1(c), by reaction of 234 mg (1.1 mmol) of 6-ethynyl-1,1,4,4,-tetramethyl-1,2,3,4-tetrahydronaphthalene, in 5 ml of THF, with 2.5 M butyllithium (0.4 ml, 1 mmol) and 2,2'-dithiobis(methyl benzoate) (267 mg; 0.8 mmol), and after purification on a column of silica (dichloromethane 30/heptane 70), the expected derivative is obtained in the form of a white solid.

¹H NMR (CDCl₃): 1.28(6H, s), 1.29(6H, s), 1.69(4H, s), 3.91(3H, s), 7.30(2H Ar, s), 7.49 to 7.54(3H Ar, m), 8.0(2H Ar, d, J=6.9 Hz).

Example 26

4-(3,5,5,8,8-Pentamethyl-5,6,7,8-tetrahydro-2-naphthylselanylethynyl)phenol (a) 4-Trimethylsilylethynylphenyl acetate In a manner similar to that of Example 1(a), starting with 4.63 g (17.7 mmol) of 4-iodophenyl acetate, 3.72 g (90%) of the expected compound are obtained in the form of a yellow powder. m.p.=45° C.

¹H NMR/CDCl₃: 0.05(s; 9H); 2.10(s, 3H); 6.84(dt, 2H); 7.28(dt, 2H).

¹³C NMR/CDCl₃: 0.00; 2*CH3/21.2; CH3/94.4; Cq/104.3; Cq/120.9; Cq/121.2; 2*CH/133.2; 2*CH/150.7; Cq/169.1; Cq.

(b) 4-5,5,8,8-Tetramethyl-5,6,7,8-tetrahydro-2-naphthylselanylethynyl)phenyl acetate In a manner similar to that of Example 4(b), after reaction of 1.39 g (2.4 mmol) of 5,5,8,8-tetramethyl-5,6,7,8-tetrahydro-2-naphthalene diselenide, in THF, with bromine (0.22 ml, 4.3 mmol), copper iodide (1.82 g, 9.6 mmol) and 4-trimethylsilylethynylphenyl acetate ester (1 g; 4.3 mmol) in DMF are added at 80° C. for 15 h, and after purification on a column of silica (dichloromethane 20/heptane 80), 220 mg (16%) of the expected derivative are obtained in the form of a yellow oil.

¹H NMR/CDCl₃: 1.19(d, 12H); 1.59(s, 4H); 2.22(s, 3H); 2.26(s, 3H); 6.97 to 7.02(m, 3H); 7.39 to 7.42(dd, 2H); 7.65(s, 1H).

¹³C NMR/CDCl₃ 19.2; CH3/19.5; CH3/30.3; 4*CH3/32.4; Cq/32.7; Cq/33.4; CH2/33.5; CH2/68.7; Cq/99.9; Cq 119.5; Cq/120.1; 2*CH/124.2; Cq/126.7; CH/126.9; C/131.0; 2*CH/133.0; Cq/142.5; Cq/143.5; Cq/138.0; Cq/167.5; Cq.

(c) 4-(3,5,5,8,8-Pentamethyl-5,6,7,8-tetrahydro-2-naphthylselanylethynyl)phenol

A mixture of 4-(5,5,8,8-tetramethyl-5,6,7,8-tetrahydro-2-napthylselanylethynyl)phenyl acetate (500 mg, 1.1 mmol) and potassium carbonate (160 mg, 1.1 mmol) in methanol (20 ml) is stirred for 24 h at room temperature and is then treated with ethyl ether and water. The organic phase is washed twice with water, dried over anhydrous magnesium sulphate and concentrated on a rotary evaporator under vacuum at 40° C. The product is purified on a column of silica (ethyl acetate 20/heptane 80). 300 mg (66%) of a clear oil are obtained.

$^1$H NMR/CDCl$_3$: 1.25 to 11.27(m, 12H); 1.66(s, 4H); 2.35(s, 3H); 6.77(d, 2H); 7.09(s, 1H); 7.38(dd, 2H); 7.73(s, 1H).

—C NMR/CDCl$_3$: 20.3; CH3/31.4; 4*CH3/33.6; 2*Cq/34.6; 2*CH2/67.2; Cq/103.7; Cq/115.3; Cq/115.6; 2*CH/127.7; Cq/128.5; 2*CH/133.0; 2*CH/133.6; Cq/143.6; Cq/143.9; Cq/156.0; Cq.

Example 27

Ethyl 4-(4-hydroxy-5,5,8,8-tetramethyl-5,6,7,8-tetrahydro-2-naphthylselanylethynyl)benzoate In a manner similar to that of Example 4(b), after reaction of 1 g (1.5 mmol) of 4-methoxymethoxy-5,5,8,8-tetramethyl-5,6,7,8-tetrahydro-2-naphthalene diselenide, in THF, with bromine (0.092 ml, 1.78 mmol), copper iodide and ethyl 4-trimethylsilylethynylbenzoate (644 mg; 2.8 mmol) in DMF are added at 80° C. for 15 h. After purification on a column of silica (dichloromethane 20/heptane 80), 220 mg (16%) of the expected derivative are obtained in the form of a yellow oil.

$^1$H NMR/CDCl$_3$: 1.29(s, 6H); 1.37 to 1.43(m, 9H); 1.65 (q, 4H); 4.39(q, 2H); 5.72(s, 1H); 7.26(s, 1H); 7.43(s, 1H); 7.55(d, 2H); 8.03(d, 2H)

Example 28

Ethyl 4-(4-methoxymethoxy-5,5,8,8-tetramethyl-5,6,7,8-tetrahydro-2-naphthylselanylethynyl)benzoate In a manner similar to that of Example 4(b), after reaction of 1 g (1.5 mmol) of 4-methoxymethoxy-5,5,8,8-tetramethyl-5,6,7,8-tetrahydro-2-naphthalene diselenide, in THF, with bromine (0.092 ml, 1.78 mmol), copper iodide and ethyl 4-trimethylsilylethynylbenzoate (644 mg 2.8 mmol) in DMF are added at 80° C. for 15 h. After purification on a column of silica (dichloromethane 20/heptane 80), 420 mg (31%) of the expected derivative are obtained in the form of a yellow oil.

$^1$H NMR/CDCl$_3$: 1.17(q, 6H); 1.31(m, 9H); 1.49 to 1.57 (m, 4H); 3.38(s, 3H); 4.25(q, 2H); 5.10(s, 2H); 7.08(d, 1H); 7.14(d, 1H); 7.41(d, 2H); 7.88(d, 2H).

Example 29

4-(4-Methoxymethoxy-5,5,8,8-tetramethyl-5,6,7,8-tetrahydro-2-naphthylselanylethynyl)benzoic acid In a manner similar to that of Example 7, by reaction of 300 mg of ethyl 4-(4-methoxymethoxy-5,5,8,8-tetramethyl-5,6,7,8-tetrahydro-2-naphthylselanylethynyl)benzoate ester in 30 ml of THF with 500 mg of sodium hydroxide, and after trituration from heptane, the expected compound is obtained in the form of a white solid.

$^1$H NMR/CDCl$_3$: 1.28 (s, 6H); 1.39 (s, 6H); 1.66 (m, 2H); 3.51 (s, 3H); 5.23 (s, 2H); 7.19 (d, 1H, J=1.8 Hz); 7.25 (d, 1H, J=1.8 Hz); 7.56 (d, 2H, J=8.5 Hz); 8.06 (d, 2H, J=8.5 Hz).

Example 30

[4-(5,5,8,8-Tetramethyl-5,6,7,8-tetrahydro-2-naphthylselanylethynyl)-phenyl]carbaldehyde A mixture of [4-(5,5,8,8-tetramethyl-5,6,7,8-tetrahydro-2-naphthylselanylethynyl)-phenyl]methanol obtained in Example 24 (280 mg, 0.7 mmol) and pyridinium dichromate (526 mg, 1.4 mmol) in dichloromethane (10 ml) is stirred at room temperature for 4 h. After filtration through silica and concentration on a rotary evaporator under vacuum at 40° C., 173 mg (63%) of the expected product are obtained in the form of a yellow oil.

$^1$H NMR/CDCl$_3$: 1.28 (s, 6H), 1.30 (s, 6H), 1.70 (s, 4H), 4.67 (s, 2H), 7.23 (1H Ar, d, J=8.3 Hz), 7.29 (1H Ar, dd, J=1.9 Hz, J=8.3 Hz), 7.52 to 7.59 (3H Ar, m), 7.84 (1H Ar, d, J=6.7 Hz); 9.99 (.H, s).

Example 31

Methyl 4-(4,4-dimethylthiochroman-8-ylselanylethynylbenzoate (a) 2-Bromo-1-(3-methylbut-2-enylthio)benzene 19.30 g (102.0 mmol) of 2-bromothiophenol, 160 ml of DMF and 15.50 g (112.0 mmol) of potassium carbonate are introduced into a three-necked flask. 13 ml (112.0 mmol) of 1-bromo-3-methyl-2-butene are added dropwise and the mixture is stirred at room temperature for two hours. The reaction medium is poured into water and extracted with ethyl acetate, and the organic phase is separated out after settling has taken place, washed with water, dried over magnesium sulphate and evaporated. 26.00 g (99%) of the expected compound are collected in the form of an orange-coloured oil.

$^1$H NMR/CDCl$_3$ d 1.65 (s, 3H), 1.73 (s, 3H), 3.56 (d, 2H, J=7.7 Hz), 5.32 (td, 1H, J=7.7/1.4 Hz), 6.96 to 7.06 (m, 1H), 7.22 to 7.26 (m, 2H), 7.52 (d, 1H, J=7.7 Hz).

(b) 4,4-Dimethyl-8-bromothiochroman 26.00 g (102.0 mmol) of 2-bromo-1-(3-methylbut-2-enylthio)benzene, 180 ml of toluene and 23.20 g (122.0 mmol) of para-toluenesulfonic acid are introduced into a three-necked flask. The reaction medium is refluxed for four hours and evaporated to dryness. The residue is taken up in aqueous sodium hydrogen carbonate solution and extracted with ethyl acetate, and the organic chase is separated out after settling has taken place, dried over magnesium sulphate and evaporated. The residue obtained is purified by chromatography on a column of silica eluted with heptane. 20.00 g (76%) of the expected compound are collected in the form of an orange-coloured oil.

$^1$H NMR (CDCl$_3$) d 1.33 (s, 6H), 1.94 (t, 2H, J=6.0 Hz), 3.04 (t, 2H, J=6.1 Hz), 6.89 (t, 1H, J=7.9 Hz), 7.34 (d, 2H, J=7.9 Hz).

(c) 4,4-Dimethyl-8-thiochromain diselenide

One crystal of iodine, magnesium (208 mg, 8.56 mmol) and a few dross of a solution of 4,4-dimethyl-8-bromothiochroman (2 g, 7.78 mmol) in ethyl ether (15 ml) are heated until the organomagnesium reagent has been initiated. The rest of the solution is then added dropwise. The reaction medium is heated for 2 h and selenium (615 mg, 7.78 mmol) is then added at room temperature. The stirring is continued for 30 min and 1N HCl solution is then added. The reaction mixture is treated with ethyl ether. The organic phase is washed twice with water, dried over anhydrous magnesium sulphate and concentrated on a rotary evaporator under vacuum at 40° C. Ethanol and sodium hydroxide are added to the oil obtained. The mixture is stirred vigorously for a few minutes and is then concentrated on a rotary evaporator under vacuum at 40° C. The product is purified on a column of silica (dichloromethane 20/heptane 80). 300 mg (15%) of a white solid are obtained.

$^1$H NMR (CDCl$_3$): 1.33 (6H, s), 1.96 (2H, m), 3.09 (2H, m), 6.93 (1H Ar, t, J=7.8 Hz), 7.26 (1H Ar, dd, J=7.8 Hz, J=1.3 Hz), 7.47 (1H Ar, dd, J=7.8 Hz, J=1.3 Hz).

(c) Methyl 4-(4,4-dimethylthiochroman-8-ylselanylethynyl)benzoate

In a manner similar to that of Example 4(b), after reaction of 300 mg (1.9 mmol) of 4,4-dimethyl-8-thiochroman diselenide, in 2 ml of THF, with bromine (0.117 ml, 2.2 mmol), cooper iodide (780 mg) and methyl 4-ethynylbenzoate (562 mg; 3.5 mmol) in 20 ml of DMF are added, and after purification on a column of silica (dichloromethane 20/heptane 80), the expected derivative is obtained in the form of a yellow solid.

$^1$H NMR (CDCl$_3$): 1.35 (6H, s), 1.97 (2H, m), 3.10 (2H, m), 3.93 (3H, s), 7.07 (1H Ar, t, J=7.8 Hz), 7.31 (1H Ar, dd, J=7.8 Hz, J=1.3 Hz), 7.55 (2H Ar, d, J=8.5 Hz) 7.59 (1H Ar, dd, J=7.8 Hz, J=1.3 Hz), 8.00 (2H Ar, d, J=8.5 Hz).

Example 32

4-(5,5,8,8-Tetramethyl-5,6,7,8-tetrahydro-2-naphthylethynylsulphanyl)benzoic acid In a manner similar to that of Example 2, by reaction of methyl 4-(5,5,8,8-tetramethyl-5,6,7,8-tetrahydro-2-naphthylethynylsulphanyl)benzoate in THF, and after crystallization from heptane, the expected derivative is obtained in the form of white solid.

$^1$NMR (CDCl$_3$): 1.28 (6H, s), 1.29 (6H, s), 1.70 (4H, s), 7.30 (2H Ar, s), 7.43 to 7.50 (3H Ar, t), 7.99 (2H Ar, d, J=7.5 Hz).

Example 33

4-(6-bromo-4,4-dimethyl-thiochroman-8-ylselanylethynyl)-benzoic Acid a) 4,4,Dimethyl-thiochroman-8-diselenide.

One crystal of iodine, magnesium (1.46 g, 60 mmol) and few drops of a solution of 4,4-dimethyl-8-bromothiochroman (10.3 g, 40 mmol) in THF (100 ml) are heated until the organomagnesium reagent has been initiated. The rest of the solution is then added dropwise. The reaction mixture is heated for 2 h and selenium (3.48 g, 44 mmol) is then added at room temperature. The stirring is continued for 2 h and 1N HCl solution is then added. The reaction mixture is treated with ethyl ether. The organic phase is washed twice with water, dried over anhydrous magnesium sulphate and concentrated on a rotary evaporator under vacuum at 40° C. Ethanol (25 ml) and sodium hydroxide (126 mg) are added to the oil obtained. The mixture is stirred vigorously for a night and is then filtered. The solid obtained is dissolved in a minimal amount of dichloromethane and then purified on silica cake.

A yellow solid is obtained. Weight 8.66 g, yield 84%.

$^1$H (CDCl$_3$): 1.33 (6H, s), 1.96 (2H, m), 3.09 (2H, m), 6.93 (1H Ar, t, J=7.8 Hz), 7.26 (1H Ar, dd, J=7.8 Hz, J=1.3 Hz), 7.47 (1H Ar, dd, J=7.8 Hz, J=1.3 Hz).

b) 6-Bromo-4,4-dimethyl-8-bromoselenythiochromane.

A bromide solution (3 ml, 58.5 mol) in CCl$_4$ (50 ml) is added dropwise to a solution of 4,4-Dimethyl-thiochromane-8-diselenide (6 g, 11.7 mmol) in CCl$_4$ (200 ml). The reaction mixture is stirred 40 h at room temperature, concentrated at a dried state on a rotary evaporator under vacuum at 40° C., then recovered in a mixture dichloromethane/heptane and concentrated again.

A clear brown powder is obtained. Weight 9.48 g. Yield 98%.

$^1$H (CDCl$_3$): 1.34 (6H, s), 1.95 (2H, m), 3.09 (2H, m), 7.43 (1H Ar, d, J=1.9 Hz), 7.66 (1H Ar, d, J=1.9 Hz).

c) Methyl-4-(6-bromo-4,4-dimethyl-thiochroman-8-ylselanylethynyl)-benzoate

Copper iodide (8.26 g, 10.8 mmol), methyl-4-ethynyl-2-hydroxybenzoate (1.73 g, 10.8 mmol) obtained according to the example 1(b) are added to a solution of 6-Bromo-4,4-dimethyl-8-bromoselenythiochromane (4.95 g, 11.9 mmol) in DMF (60 ml). the reaction mixture is stirred at room temperature for 20 h, then treated with ethyl ether and ammoniac solution. The organic phase is washed twice with water, dried over anhydrous magnesium sulphate and concentrated on a rotary evaporator under vacuum at 40° C. The product is purified on fast plug with a solvent gradient based on heptane-ethylacetate.

Clear brown powder. Weight 3.38 g. Yield 63%.

$^1$H (CDCl$_3$): 1.34 (6H, s), 1.95 (2H, m), 3.10 (2H, m), 3.93 (3H, s), 7.40 (1H Ar, d, J=2.0 Hz), 7.54 (2H Ar, dd, J=1.7 Hz, J=6.7 Hz), 7.74 (1H Ar, d, J=2.0 Hz), 8.02 (2H Ar, dd, J=1.7 Hz, J=6.7 Hz).

d) 4-(6-bromo-4,4-dimethyl-thiochroman-8-ylselanylethynyl)-benzoic Acid.

In a manner similar to that of Example 5, with 395 mg (0.8 mmol.) of methyl 4-(6-bromo-4,4-dimethyl-thiochroman-8-ylselanycethynyl)-benzoate, the expected acid is obtained in the form of a white powder. Weight 192 mg. Yield 50%.

$^1$H (CDCl$_3$): 1.29 (6H, s), 1.96 (2H, m), 3.11 (2H, m), 3.93 (3H, s), 7.40 (1H Ar, d, J=1.9 Hz), 7.55 (2H Ar, d, J=8.3 Hz), 7.73 (1H Ar, d, J=1.9 Hz), 8.04 (2H Ar, d, J=8.3 Hz).

$^-$C (CDCl$_3$): 24.11 (CH2), 29.84 (2 CH3), 33.83 (C), 33.80 (CH2), 72.75 (C), 104.27 (C), 118.46 (C), 128.01 (C), 127.97 (CH), 128.98 (C), 129.21 (CH), 129.79 (2CH), 131.20 (2CH), 145.26 (C), 167.83 (C).

Formulation Examples

Example 1

Various pharmaceutical and cosmetic formulations based on the compounds according to the invention are described below.

A—Oral Route

| (a) 0.2 g tablet | |
|---|---|
| Compound of Example 1 | 10.001 g |
| Starch | 0.114 g |
| Dicalcium phosphate | 0.020 g |
| Silica | 0.020 g |
| Lactose | 0.030 g |
| Talc | 0.010 g |
| Magnesium stearate | 0.005 g |

In this example, the compound of Example 1 can be replaced with the same amount of one of the compounds of Examples 4, 6, 11, 13 or 15.

| (b) Drinkable suspension in 5 ml vials | |
|---|---|
| Compound of Example 3 | 20.001 g |
| Glycerol | 0.500 g |
| 70% sorbitol | 0.500 g |
| Sodium saccharinate | 0.010 g |

|                             |          |
|-----------------------------|----------|
| Methyl p-hydroxybenzoate    | 0.040 g  |
| Flavouring, qs              |          |
| Purified water qs           | 5 ml     |

(c) 0.8 g tablet

|                          |         |
|--------------------------|---------|
| Compound of Example 2    | 0.500 g |
| Pregelatinized starch    | 0.100 g |
| Microcrystalline cellulose | 0.115 g |
| Lactose                  | 0.075 g |
| Magnesium stearate       | 0.010 g |

In this example, the compound according to Example 2 can be replaced with the same amount of one of the compounds of Examples 6, 11, 14 or 28.

(d) Drinkable suspension in 10 ml vials

|                          |         |
|--------------------------|---------|
| Compound of Example 3    | 0.200 g |
| Glycerol                 | 1.000 g |
| 70% sorbitol             | 1.000 g |
| Sodium saccharinate      | 0.010 g |
| Methyl p-hydroxybenzoate | 0.080 g |
| Flavouring, qs           |         |
| Purified water qs        | 10 ml   |

B—Topical Route

(a) Ointment

|                                |          |
|--------------------------------|----------|
| Compound of Example 2          | 20.020 g |
| Isopropyl myristate            | 81.700 g |
| Fluid liquid petroleum jelly   | 9.100 g  |
| Silica ("Aerosil 200" sold by Degussa) | 9.180 g |

(b) Ointment

|                           |         |
|---------------------------|---------|
| Compound of Example 1     | 0.300 g |
| White petroleum jelly codex | 100 g |

(c) Nonionic water-in-oil cream

|                           |          |
|---------------------------|----------|
| Compound of Example 1     | 0.100 g  |
| Mixture of emulsifying lanolin alcohols, waxes and oils ("anhydrous eucerin" sold by BDF) | 39.900 g |
| Methyl p-hydroxybenzoate  | 0.075 g  |
| Propyl p-hydroxybenzoate  | 0.075 g  |
| Sterile demineralized water qs | 100 g |

In this example, the compound according to Example 1 can be replaced with the same amount of one or the compounds of Examples 4, 16, 22, 27 or 32.

(d) Lotion

|                              |          |
|------------------------------|----------|
| Compound of Example 3        | 0.100 g  |
| Polyethylene glycol (PEG-400)| 69.900 g |
| 95% ethanol                  | 30.000 g |

(e) Hydrophobic ointment

|                                          |          |
|------------------------------------------|----------|
| Compound of Example 1                    | 0.300 g  |
| Isopropyl myristate                      | 36.400 g |
| Silicone oil ("Rhodorsil 47V300" sold by Rhone-Poulenc) | 36.400 g |
| Beeswax                                  | 13.600 g |
| Silicone oil ("Abil 300.000 cst" sold by Goldschmidt) | 100 g |

(f) Nonionic oil-in-water cream

|                           |           |
|---------------------------|-----------|
| Compound of Example 2     | 1.000 g   |
| Cetyl alcohol             | 4.000 g   |
| Glyceryl monostearate     | 2.500 g   |
| PEG stearate              | 502.500 g |
| Karite butter             | 9.200 g   |
| Propylene glycol          | 12.000 g  |
| Methyl p-hydroxybenzoate  | 0.075 g   |
| Propyl p-hydroxybenzoate  | 0.075 g   |
| Sterile demineralized water | 100 g   |

In this example, the compound according to Example 2 can be replaced with the same amount of one of the compounds of Examples 5, 9, 12, 19 and 32.

Test of Activity

Results of differentiation tests on mouse embryonic teratocarcinoma cells (F9) to identify the RAR-agonist molecules as described in Skin Pharmacol. 3, pp. 256–267, 1990.

After treatment with the compounds of the examples cited in the following table, the mouse embryonic teratocarcinoma F9 cells differentiate into endodermal cells. This differentiation is characterized by the secretion of the plasminogen activator into the culture medium.

The activity of the product is expressed by the $AC_{50}$ value representing the concentration of the test product which produces half of the maximum amount of plasminogen activator secreted.

| Examples    | F9 $AC_{50}$ (nM) |
|-------------|-------------------|
| Compound 1  | 20                |
| Compound 2  | 1                 |
| Compound 4  | 4                 |
| Compound 5  | 21                |
| Compound 16 | 33                |
| Compound 18 | 34                |

These results indicate that the compounds of Examples 1, 2, 4, 5, 16 and 18 are RAR-agonist compounds.

TABLE A
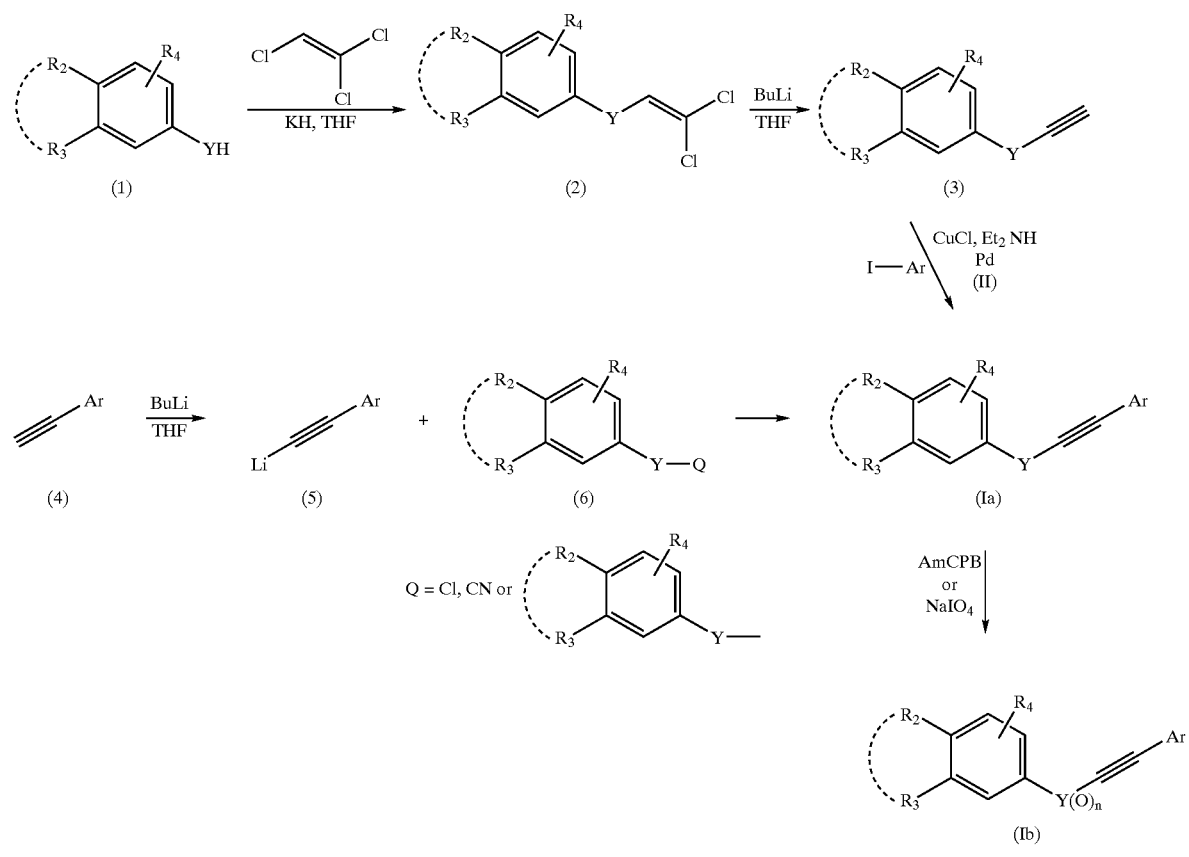
n = 0 if Y is oxygen
TABLE B
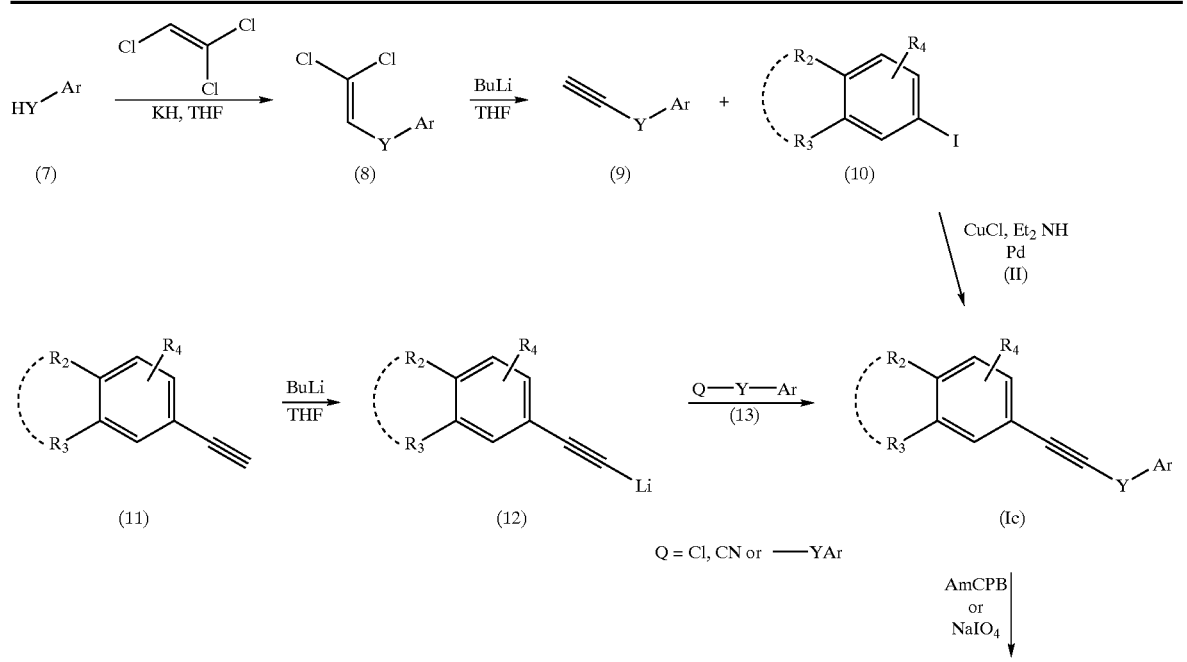

TABLE B-continued

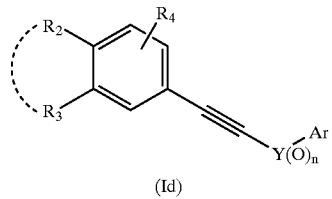

(Id)

n = 0 if Y is oxygen

What is claimed is:

1. Bi-aromatic compounds linked via a heteroethynylene bond, corresponding to the general formula (I) below:

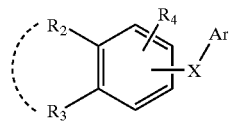
(I)

in which:

Ar represents the formula (a) below:

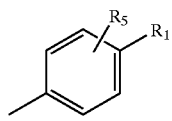
(a)

$R_1$ represents a halogen atom, —$CH_3$, —$CH_2$—$OR_7$, —$OR_7$, —$COR_8$ or a polyether radical, $R_2$ and $R_3$, taken together, form a 5- or 6-membered ring, optionally substituted with at least one methyl and interrupted by a hetero atom chosen from O and S, $R_4$ and $R_5$ represent H, a halogen atom, linear or branched $C_1$–$C_{20}$ alkyl, —$OR_7$ or a polyether radical, $R_7$ represents H, linear or branched $C_1$–$C_{10}$ alkyl or —$COR_g$, $R_8$ represents H, linear or branched $C_1$–$C_{10}$, alkyl, —$OR_{10}$ or

$R_9$ represents linear or branched $C_1$–$C_{10}$ alkyl, $R_{10}$ represents H, linear or branched $C_1$–$C_{20}$ alkyl, mono- or polyhydroxyalkyl, allyl, optionally substituted aryl or aralkyl, or a sugar residue, r' and r", which may be identical or different, represent H, $C_1$–$C_{10}$ alkyl, mono- or polyhydroxyalkyl, optionally substituted aryl, an amino acid or peptide residue, or, taken together with the nitrogen atom, form a heterocycle, X represents a divalent radical which, from right to left or vice-versa, has the formula:

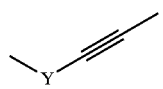

in which:

Y represents O, $S(O)_n$ or $Se(O)_{n'}$, n and n' being 0, 1 or 2, and the salts of the compounds of formula (I) when $R_1$ represents a carboxylic acid function, as well as the optical isomers of the said compounds of formula (I).

2. Compounds according to claim 1, in the form of a salt of an alkali metal or alkaline-earth metal, or alternatively of zinc or of an organic amine.

3. Compounds according to claim 1, wherein the $C_1$–$C_{10}$ alkyl radical is chosen from the group consisting of the methyl, ethyl, isopropyl, butyl, tert-butyl, hexyl, 2-ethylhexyl and octyl radicals.

4. Compounds according to claim 1, wherein the linear or branched $C_1$–$C_{20}$ alkyl radical is chosen from the group consisting of the methyl, ethyl, propyl, 2-ethylhexyl, octyl, dodecyl, hexadecyl and octadecyl radicals.

5. Compounds according to claim 1, wherein the polyether radical is chosen from the group consisting of the methoxymethoxy, methoxyethoxy and methoxyethoxymethoxy radicals.

6. Compounds according to claim 1, wherein the monohydroxyalkyl radical is chosen from the group consisting of the 2-hydroxyethyl, 2-hydroxypropyl and 3-hydroxypropyl radicals.

7. Compounds according to claim 1, wherein the polyhydroxyalkyl radical is chosen from the group consisting of the 2,3-dihydroxypropyl, 2,3,4-trihydroxybutyl, 2,3,4,5-tetrahydroxypentyl radicals and the pentaerythritol residue.

8. Compounds according to claim 1, wherein the aryl radical is a phenyl radical optionally substituted with at least one halogen atom, a hydroxyl or a nitro function.

9. Compounds according to claim 1, wherein the aralkyl radical is chosen from the group consisting of the benzyl and phenethyl radicals optionally substituted with at least one halogen atom, a hydroxyl or a nitro function.

10. Compounds according to claim 1, wherein the sugar residue is chosen from the group consisting of the glucose, galactose, mannose and glucuronic acid residues.

11. Compounds according to claim 1, wherein the amino acid residue is chosen from the group consisting of the residues derived from lysine, from glycine or from aspartic acid.

12. Compounds according to claim 1, wherein the heterocyclic radical is chosen from the group consisting of piperidino, morpholino, pyrrolidino and piperazino radicals, optionally substituted in position 4 with a $C_1$–$C_6$ alkyl or a mono- or polyhydroxyalkyl.

13. Compounds according to claim 1, wherein the halogen atom is chosen from the group consisting of fluorine, chlorine and bromine.

14. Compounds according to claim 1, corresponding to the following general formula

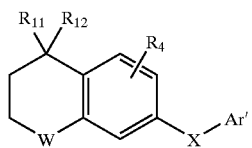

(III)

in which:

W represents O or S,

Ar' is Ar, and $R_{11}$ and $R_{12}$, which may be identical or different, represent H or —$OH_3$.

15. A compound selected from the group consisting of:

Methyl 4-(4,4-dimethylthiochroman-8-ylselanylethynyl) benzoate, 4-(4,4-Dimethylthiochroman-8-ylselanylethynyl)benzoic acid, and 4-(6-bromo-4,4-dimethyl-thiochroman-8-ylselanylethynyl)-benzoic acid.

16. A method of preparing a pharmaceutical composition comprising mixing a compound according to claim 1 with a medicinal medium.

17. Pharmaceutical composition comprising a pharmaceutically acceptable medium and at least one compound according to claim 1.

18. Cosmetic composition comprising a cosmetically acceptable medium and at least one compound according to claim 1.

19. Composition according to claim 18, wherein the concentration of said at least one compound is between 0.001 and 3% by weight relative to the total weight of the composition.

20. Composition according to claim 18, wherein the concentration of said at least one compound is between 0.001% and 5% by weight relative t the total weight of the composition.

* * * * *